US011821020B2

(12) United States Patent
Whalen et al.

(10) Patent No.: US 11,821,020 B2
(45) Date of Patent: Nov. 21, 2023

(54) ENZYMATIC PROCESS FOR PRODUCTION OF MODIFIED HOP PRODUCTS

(71) Applicant: KALAMAZOO HOLDINGS, INC., Kalamazoo, MI (US)

(72) Inventors: Katie Whalen, Charlottesville, VA (US); Donald Richard Berdahl, Lawton, MI (US); Brian Patrick Buffin, Yakima, WA (US); Matthew Blake Jones, Portage, MI (US); Katrina Williams, Riner, VA (US)

(73) Assignee: KALAMAZOO HOLDINGS, INC., Kalamazoo, MI (US)

( * ) Notice: Subject to any disclaimer, the term of this patent is extended or adjusted under 35 U.S.C. 154(b) by 189 days.

(21) Appl. No.: 17/362,070

(22) Filed: Jun. 29, 2021

(65) Prior Publication Data

US 2021/0355510 A1    Nov. 18, 2021

Related U.S. Application Data

(62) Division of application No. 16/584,058, filed on Sep. 26, 2019, now abandoned.

(60) Provisional application No. 62/736,558, filed on Sep. 26, 2018.

(51) Int. Cl.
*C12P 7/38* (2006.01)
*C12C 3/12* (2006.01)
*C12N 11/16* (2006.01)

(52) U.S. Cl.
CPC ....... *C12P 7/38* (2013.01); *C12C 3/12* (2013.01); *C12N 11/16* (2013.01); *C12Y 101/01086* (2013.01)

(58) Field of Classification Search
CPC .. C12P 7/38; C12P 7/50; C12Y 101/01; C12N 11/16
See application file for complete search history.

(56) References Cited

U.S. PATENT DOCUMENTS

| | | | |
|---|---|---|---|
| 2,433,411 | A | 12/1947 | Wallerstein |
| 3,044,879 | A | 7/1962 | Koch et al. |
| 5,624,701 | A | 4/1997 | Maye et al. |
| 6,748,849 | B2 | 6/2004 | Wilson et al. |
| 7,087,256 | B2 | 8/2006 | Gimbel et al. |
| 8,426,178 | B2 | 4/2013 | Savile et al. |
| 10,961,550 | B2* | 3/2021 | Whalen ............... C12P 7/38 |
| 11,591,625 | B2* | 2/2023 | Whalen .......... C12Y 101/01184 |
| 2002/0045233 | A1 | 4/2002 | Hershberger et al. |
| 2004/0115290 | A1 | 6/2004 | Tripp |
| 2013/0177962 | A1 | 7/2013 | Savile et al. |
| 2020/0095618 | A1 | 3/2020 | Whalen et al. |

FOREIGN PATENT DOCUMENTS

| | | |
|---|---|---|
| EP | 0924294 | 6/1999 |
| WO | WO2004082697 | 9/2004 |
| WO | WO2009029554 | 3/2009 |
| WO | WO2009077611 | 6/2009 |
| WO | WO 2010/025238 | 3/2010 |
| WO | WO2011059486 | 5/2011 |
| WO | WO 2020/069139 | 4/2020 |
| WO | WO 2021/061915 | 4/2021 |

OTHER PUBLICATIONS

NCBI Reference Sequence Accession No. WP_002357438.1, Jul. 15, 2020.
NCBI Reference Sequence Accession No. WP_002552216.1, Sep. 25, 2015.
NCBI Reference Sequence Accession No. WP_004082240.1, Oct. 27, 2015.
NCBI Reference Sequence Accession No. WP_004083050.1, Apr. 17, 2020.
NCBI Reference Sequence Accession No. WP_010970802.1, May 14, 2017.
NCBI Reference Sequence Accession No. XP_016221599.1, Jun. 24, 2016.
NCBI Reference Sequence Accession No. XP_018658847.1, Apr. 4, 2018.
NCBI Reference Sequence Accession No. XP_024546983.1, Apr. 17, 2018.
International Search Report for PCT/US2020/052396 dated Mar. 25, 2021.
Accession No. Q9X248, 2000.
De Keuxeleire, Denis, "Fundamentals of beer and hop chemistry", Quimica Nova, 23(1), 2000, pp. 108-112.
Digmdonno, Lidia, et al., "Brewing with prolyl endopeptidase from Aspergillus niger: the impact of enzyetic treatment on gluten levels, quality attributes and sensory profile", International Journal of Food Science & Technology, 52, Mar. 2017, pp. 1367-1374.
Gros, Jagues, et al., "Enzymatic release of odourant polyfunctional thiols from cysteine conjugates in hop", J. Inst. Brew. 2013, 119 (4), 223-227.
Hult, Karl, et al., "Enzyme promiscuity: mechanism and applications", Trends in Biotechnology, vol. 25, No. 5, pp. 231-238.
International Search Report for PCT/US2016/053117 dated Feb. 4, 2020.
International Search Report for PCT/US2019/053170 dated Mar. 23, 2020.
Nobeli, Irene, et al., "Protein promiscuity and its implications for biotechnology", Nature Biotechnology, vol. 27, No. 2, Feb. 2009, pp. 157-167.
Partial international search report for PCT/US2019/053176 dated Jan. 29, 2020.

(Continued)

*Primary Examiner* — Tekchand Saidha
(74) *Attorney, Agent, or Firm* — HUESCHEN AND SAGE

(57) ABSTRACT

The present invention relates to a process for producing a beer tittering agent via enzyme catalyzed bioconversion of hop-derived isoalpha acids to dihydro-(rho)-isoalpha acids and to the novel enzyme catalysts which may be employed in such a process.

17 Claims, 8 Drawing Sheets

Specification includes a Sequence Listing.

(56) References Cited

OTHER PUBLICATIONS

Pozen, Morris, A., "Enzymes in brewing", Industrial and Engineering Chemistry, vol. 26, No. 11, Nov. 1934, pp. 1127-1133.
Prast, Tatiana, et al., "Biotransformations of hop-derived aroma compounds by *Saccharomyces cerevisiae* upon fermentation", Cerevisia 36, 2012, pp. 125-132.
Robinson, Peter , K, "Enzymes: principles and biotechnological applications", Essays Biochem., 59, 2015, pp. 1-41.
Safety Data Sheet for Sodium Borohydride, SIGMA-ALDRICH, Version 6.5, Jan. 2020, pp. 1-18.
Terfebr, D., et al., Accession No. A0A0865TY, 2014.
Huvaere, et al., Photochem. Photobiol. Sci. 2004, 3, 854-858.
Redihop® product information, Jun. 8, 2020.
Reduced Isolone® product information (https:www.kalsec.com/hop-acids).
Todd, et al., MBAA Tech. Quart., 1996, 33, 91-95.
Verzele, et al.. J. Inst. Brew., 1986, 92, 32-48.

* cited by examiner

Figure 1. Enzyme catalyzed reduction of a representative epimer of isoalpha acids.

Figure 2. SDS-PAGE analysis of all purified reductases.

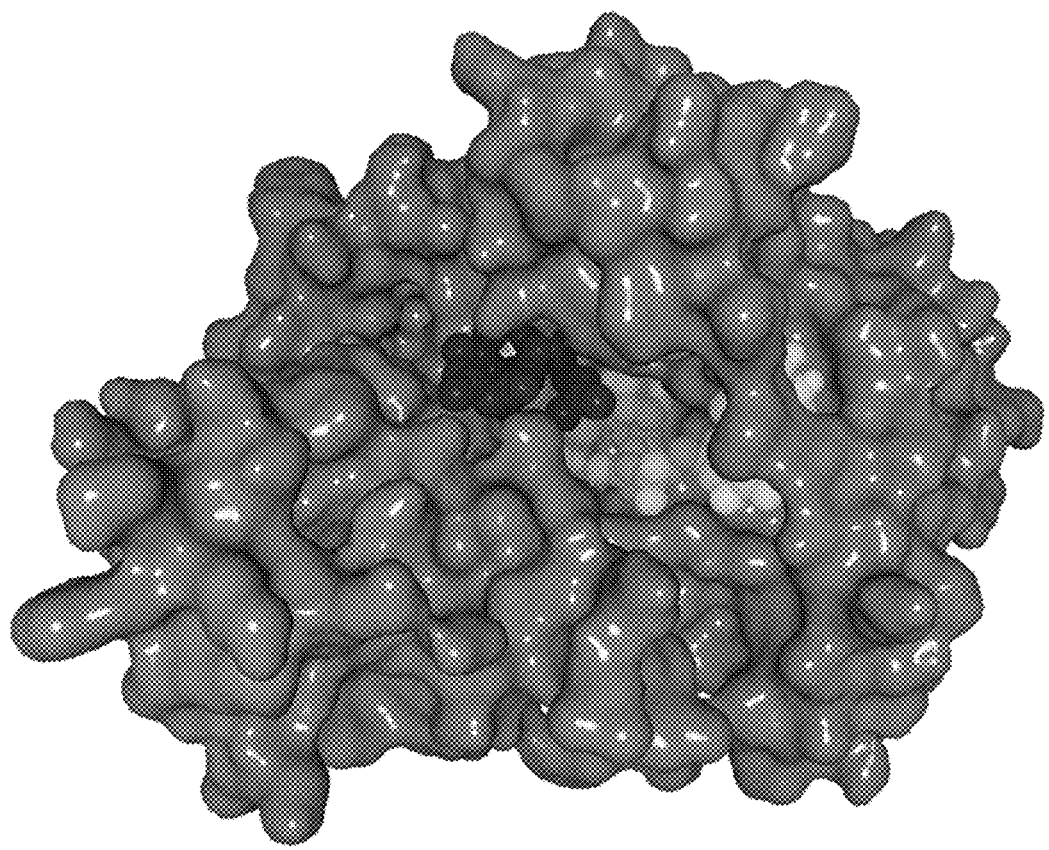
Figure 4 – Structural model of reductase R17

Figure 6. Clustal Omega amino acid sequence alignment of active ketoreductase homologs: R4, R17, R20, R21, and R23

SEQUENCE LISTING

<160> NUMBER OF SEQ ID NOS: 22

<210> SEQ ID NO 1
<211> LENGTH: 277
<212> TYPE: PRT
<213> ORGANISM: Homo sapiens

<400> SEQUENCE: 1

Met Ser Ser Gly Ile His Val Ala Leu Val Thr Gly Gly Asn Lys Gly
1               5                   10                  15

Ile Gly Leu Ala Ile Val Arg Asp Leu Cys Arg Leu Phe Ser Gly Asp
            20                  25                  30

Val Val Leu Thr Ala Arg Asp Val Thr Arg Gly Gln Ala Ala Val Gln
        35                  40                  45

Gln Leu Gln Ala Glu Gly Leu Ser Pro Arg Phe His Gln Leu Asp Ile
    50                  55                  60

Asp Asp Leu Gln Ser Ile Arg Ala Leu Arg Asp Phe Leu Arg Lys Glu
65                  70                  75                  80

Tyr Gly Gly Leu Asp Val Leu Val Asn Asn Ala Gly Ile Ala Phe Lys
                85                  90                  95

Val Ala Asp Pro Thr Pro Phe His Ile Gln Ala Glu Val Thr Met Lys
            100                 105                 110

Thr Asn Phe Phe Gly Thr Arg Asp Val Cys Thr Glu Leu Leu Pro Leu
        115                 120                 125

Ile Lys Pro Gln Gly Arg Val Val Asn Val Ser Ser Ile Met Ser Val
    130                 135                 140

Arg Ala Leu Lys Ser Cys Ser Pro Glu Leu Gln Gln Lys Phe Arg Ser
145                 150                 155                 160

Glu Thr Ile Thr Glu Glu Leu Val Gly Leu Met Asn Lys Phe Val
                165                 170                 175

Glu Asp Thr Lys Lys Gly Val His Gln Lys Glu Gly Trp Pro Ser Ser
            180                 185                 190

Ala Tyr Gly Val Thr Lys Ile Gly Val Thr Val Leu Ser Arg Ile His
        195                 200                 205

Ala Arg Lys Leu Ser Glu Gln Arg Lys Gly Asp Lys Ile Leu Leu Asn
    210                 215                 220

Ala Cys Cys Pro Gly Trp Val Arg Thr Asp Met Ala Gly Pro Lys Ala
225                 230                 235                 240

Thr Lys Ser Pro Glu Glu Gly Ala Glu Thr Pro Val Tyr Leu Ala Leu
                245                 250                 255

Leu Pro Pro Asp Ala Glu Gly Pro His Gly Gln Phe Val Ser Glu Lys
            260                 265                 270

Arg Val Glu Gln Trp
        275

<210> SEQ ID NO 2
<211> LENGTH: 246
<212> TYPE: PRT
<213> ORGANISM: Thermotoga maritima

<400> SEQUENCE: 2

Met Arg Leu Glu Gly Lys Val Cys Leu Ile Thr Gly Ala Ala Ser Gly
1               5                   10                  15

Ile Gly Lys Ala Thr Thr Leu Leu Phe Ala Gln Glu Gly Ala Thr Val
            20                  25                  30

Ile Ala Gly Asp Ile Ser Lys Glu Asn Leu Asp Ser Leu Val Lys Glu

```
                  35                  40                  45
Ala Glu Gly Leu Pro Gly Lys Val Asp Pro Tyr Val Leu Asn Val Thr
 50                  55                  60

Asp Arg Asp Gln Ile Lys Glu Val Val Glu Lys Val Val Gln Lys Tyr
 65                  70                  75                  80

Gly Arg Ile Asp Val Leu Val Asn Asn Ala Gly Ile Thr Arg Asp Ala
                 85                  90                  95

Leu Leu Val Arg Met Lys Glu Glu Asp Trp Asp Ala Val Ile Asn Val
                100                 105                 110

Asn Leu Lys Gly Val Phe Asn Val Thr Gln Met Val Val Pro Tyr Met
                115                 120                 125

Ile Lys Gln Arg Asn Gly Ser Ile Val Asn Val Ser Ser Val Val Gly
130                 135                 140

Ile Tyr Gly Asn Pro Gly Gln Thr Asn Tyr Ala Ala Ser Lys Ala Gly
145                 150                 155                 160

Val Ile Gly Met Thr Lys Thr Trp Ala Lys Glu Leu Ala Gly Arg Asn
                165                 170                 175

Ile Arg Val Asn Ala Val Ala Pro Gly Phe Ile Glu Thr Pro Met Thr
                180                 185                 190

Glu Lys Leu Pro Glu Lys Ala Arg Glu Thr Ala Leu Ser Arg Ile Pro
                195                 200                 205

Leu Gly Arg Phe Gly Lys Pro Glu Glu Val Ala Gln Val Ile Leu Phe
210                 215                 220

Leu Ala Ser Asp Glu Ser Ser Tyr Val Thr Gly Gln Val Ile Gly Ile
225                 230                 235                 240

Asp Gly Gly Leu Val Ile
                245

<210> SEQ ID NO 3
<211> LENGTH: 342
<212> TYPE: PRT
<213> ORGANISM: Saccharomyces cerevisiae

<400> SEQUENCE: 3

Met Ser Val Phe Val Ser Gly Ala Asn Gly Phe Ile Ala Gln His Ile
 1               5                  10                  15

Val Asp Leu Leu Leu Lys Glu Asp Tyr Lys Val Ile Gly Ser Ala Arg
                20                  25                  30

Ser Gln Glu Lys Ala Glu Asn Leu Thr Glu Ala Phe Gly Asn Asn Pro
                35                  40                  45

Lys Phe Ser Met Glu Val Val Pro Asp Ile Ser Lys Leu Asp Ala Phe
 50                  55                  60

Asp His Val Phe Gln Lys His Gly Lys Asp Ile Lys Ile Val Leu His
 65                  70                  75                  80

Thr Ala Ser Pro Phe Cys Phe Asp Ile Thr Asp Ser Glu Arg Asp Leu
                 85                  90                  95

Leu Ile Pro Ala Val Asn Gly Val Lys Gly Ile Leu His Ser Ile Lys
                100                 105                 110

Lys Tyr Ala Ala Asp Ser Val Glu Arg Val Val Leu Thr Ser Ser Tyr
                115                 120                 125

Ala Ala Val Phe Asp Met Ala Lys Glu Asn Asp Lys Ser Leu Thr Phe
                130                 135                 140

Asn Glu Glu Ser Trp Asn Pro Ala Thr Trp Glu Ser Cys Gln Ser Asp
145                 150                 155                 160
```

-continued

```
Pro Val Asn Ala Tyr Cys Gly Ser Lys Lys Phe Ala Glu Lys Ala Ala
            165                 170                 175

Trp Glu Phe Leu Glu Glu Asn Arg Asp Ser Val Lys Phe Glu Leu Thr
        180                 185                 190

Ala Val Asn Pro Val Tyr Val Phe Gly Pro Gln Met Phe Asp Lys Asp
        195                 200                 205

Val Lys Lys His Leu Asn Thr Ser Cys Glu Leu Val Asn Ser Leu Met
    210                 215                 220

His Leu Ser Pro Glu Asp Lys Ile Pro Glu Leu Phe Gly Gly Tyr Ile
225                 230                 235                 240

Asp Val Arg Asp Val Ala Lys Ala His Leu Val Ala Phe Gln Lys Arg
                245                 250                 255

Glu Thr Ile Gly Gln Arg Leu Ile Val Ser Glu Ala Arg Phe Thr Met
            260                 265                 270

Gln Asp Val Leu Asp Ile Leu Asn Glu Asp Phe Pro Val Leu Lys Gly
        275                 280                 285

Asn Ile Pro Val Gly Lys Pro Gly Ser Gly Ala Thr His Asn Thr Leu
    290                 295                 300

Gly Ala Thr Leu Asp Asn Lys Lys Ser Lys Lys Leu Leu Gly Phe Lys
305                 310                 315                 320

Phe Arg Asn Leu Lys Glu Thr Ile Asp Thr Ala Ser Gln Ile Leu
                325                 330                 335

Lys Phe Glu Gly Arg Ile
            340

<210> SEQ ID NO 4
<211> LENGTH: 272
<212> TYPE: PRT
<213> ORGANISM: Cytophaga hutchinsonii

<400> SEQUENCE: 4

Met Asn Gln Val Val Leu Val Thr Gly Gly Ser Gly Ile Gly Lys
1               5                   10                  15

Ser Ile Cys Leu Tyr Leu His Glu Lys Gly Tyr Ile Val Tyr Gly Thr
            20                  25                  30

Ser Arg Asn Pro Ala Arg Tyr Ala His Glu Val Pro Phe Lys Leu Ile
        35                  40                  45

Ala Leu Asp Val Leu Asp Asp Thr Thr Ile Thr Pro Ala Leu Lys Thr
    50                  55                  60

Ile Ile Asp Ala Glu Gly Lys Leu Asp Val Leu Val Asn Asn Ala Gly
65                  70                  75                  80

Ile Gly Met Leu Gly Ser Ile Glu Asp Ser Thr Ala Glu Glu Val Lys
                85                  90                  95

Glu Val Phe Glu Thr Asn Val Tyr Gly Ile Leu Arg Thr Cys Gln Ala
            100                 105                 110

Val Leu Pro His Met Arg Glu Arg Lys Met Gly Leu Ile Ile Asn Val
        115                 120                 125

Ser Ser Ile Ala Gly Tyr Met Gly Leu Pro Tyr Arg Gly Ile Tyr Ser
    130                 135                 140

Ala Thr Lys Ala Ser Val His Met Ile Thr Glu Ala Met Arg Met Glu
145                 150                 155                 160

Leu Lys Pro Tyr Gly Val His Ala Cys Val Val Asp Pro Gly Asp Phe
                165                 170                 175

Ala Thr Asn Ile Ser Asp Asn Arg Lys Val Ala His Ala Gly Arg Ser
            180                 185                 190
```

```
Gly Ser Val Tyr Met Glu Glu Ile Asn Arg Ile Glu Ala Met Ile Asn
            195                 200                 205

Ala Glu Val Ala His Ser Ser Asp Pro Leu Leu Met Gly Lys Ala Ile
210                 215                 220

Glu Lys Ile Ile Arg Ser Ser Asn Pro Asp Ile Asn Tyr Leu Val Gly
225                 230                 235                 240

Lys Pro Met Gln Lys Leu Ser Ile Leu Val Arg Arg Leu Val Pro Lys
                245                 250                 255

Lys Trp Phe Glu Lys Ile Ile Ala Ser His Tyr Asn Met Pro Val Lys
            260                 265                 270

<210> SEQ ID NO 5
<211> LENGTH: 326
<212> TYPE: PRT
<213> ORGANISM: Arabidopsis thaliana

<400> SEQUENCE: 5

Met Ala Asn Ser Gly Glu Gly Lys Val Val Cys Val Thr Gly Ala Ser
1               5                   10                  15

Gly Tyr Ile Ala Ser Trp Leu Val Lys Phe Leu Leu Ser Arg Gly Tyr
            20                  25                  30

Thr Val Lys Ala Ser Val Arg Asp Pro Ser Asp Pro Lys Lys Thr Gln
        35                  40                  45

His Leu Val Ser Leu Glu Gly Ala Lys Glu Arg Leu His Leu Phe Lys
    50                  55                  60

Ala Asp Leu Leu Glu Gln Gly Ser Phe Asp Ser Ala Ile Asp Gly Cys
65                  70                  75                  80

His Gly Val Phe His Thr Ala Ser Pro Phe Phe Asn Asp Ala Lys Asp
                85                  90                  95

Pro Gln Ala Glu Leu Ile Asp Pro Ala Val Lys Gly Thr Leu Asn Val
            100                 105                 110

Leu Asn Ser Cys Ala Lys Ala Ser Ser Val Lys Arg Val Val Val Thr
        115                 120                 125

Ser Ser Met Ala Ala Val Gly Tyr Asn Gly Lys Pro Arg Thr Pro Asp
130                 135                 140

Val Thr Val Asp Glu Thr Trp Phe Ser Asp Pro Glu Leu Cys Glu Ala
145                 150                 155                 160

Ser Lys Met Trp Tyr Val Leu Ser Lys Thr Leu Ala Glu Asp Ala Ala
                165                 170                 175

Trp Lys Leu Ala Lys Glu Lys Gly Leu Asp Ile Val Thr Ile Asn Pro
            180                 185                 190

Ala Met Val Ile Gly Pro Leu Leu Gln Pro Thr Leu Asn Thr Ser Ala
        195                 200                 205

Ala Ala Ile Leu Asn Leu Ile Asn Gly Ala Lys Thr Phe Pro Asn Leu
    210                 215                 220

Ser Phe Gly Trp Val Asn Val Lys Asp Val Ala Asn Ala His Ile Gln
225                 230                 235                 240

Ala Phe Glu Val Pro Ser Ala Asn Gly Arg Tyr Cys Leu Val Glu Arg
                245                 250                 255

Val Val His His Ser Glu Ile Val Asn Ile Leu Arg Glu Leu Tyr Pro
            260                 265                 270

Asn Leu Pro Leu Pro Glu Arg Cys Val Asp Glu Asn Pro Tyr Val Pro
        275                 280                 285

Thr Tyr Gln Val Ser Lys Asp Lys Thr Arg Ser Leu Gly Ile Asp Tyr
```

```
                290                 295                 300
Ile Pro Leu Lys Val Ser Ile Lys Glu Thr Val Ser Leu Lys Glu
305                 310                 315                 320

Lys Gly Phe Ala Gln Phe
                325

<210> SEQ ID NO 6
<211> LENGTH: 236
<212> TYPE: PRT
<213> ORGANISM: Pseudomonas savastanoi

<400> SEQUENCE: 6

Met Thr Leu Ser Ser Ala Pro Ile Leu Ile Thr Gly Ala Ser Gln Arg
1               5                   10                  15

Val Gly Leu His Cys Ala Leu Arg Leu Leu Glu His Gly His Arg Val
                20                  25                  30

Ile Ile Ser Tyr Arg Thr Glu His Ala Ser Val Thr Glu Leu Arg Gln
            35                  40                  45

Ala Gly Ala Val Ala Leu Tyr Gly Asp Phe Ser Cys Glu Thr Gly Ile
    50                  55                  60

Met Ala Phe Ile Asp Leu Leu Lys Thr Gln Thr Ser Ser Leu Arg Ala
65                  70                  75                  80

Val Val His Asn Ala Ser Glu Trp Leu Ala Glu Thr Pro Gly Glu Glu
                85                  90                  95

Ala Asp Asn Phe Thr Arg Met Phe Ser Val His Met Leu Ala Pro Tyr
                100                 105                 110

Leu Ile Asn Leu His Cys Glu Pro Leu Leu Thr Ala Ser Glu Val Ala
            115                 120                 125

Asp Ile Val His Ile Ser Asp Asp Val Thr Arg Lys Gly Ser Ser Lys
    130                 135                 140

His Ile Ala Tyr Cys Ala Thr Lys Ala Gly Leu Glu Ser Leu Thr Leu
145                 150                 155                 160

Ser Phe Ala Ala Arg Phe Ala Pro Leu Val Lys Val Asn Gly Ile Ala
                165                 170                 175

Pro Ala Leu Leu Met Phe Gln Pro Lys Asp Asp Ala Ala Tyr Arg Ala
                180                 185                 190

Asn Ala Leu Ala Lys Ser Ala Leu Gly Ile Glu Pro Gly Ala Glu Val
            195                 200                 205

Ile Tyr Gln Ser Leu Arg Tyr Leu Leu Asp Ser Thr Tyr Val Thr Gly
    210                 215                 220

Thr Thr Leu Thr Val Asn Gly Gly Arg His Val Lys
225                 230                 235

<210> SEQ ID NO 7
<211> LENGTH: 246
<212> TYPE: PRT
<213> ORGANISM: Pseudomonas putida

<400> SEQUENCE: 7

Met Ser Leu Gln Gly Lys Val Ala Leu Val Thr Gly Ala Ser Arg Gly
1               5                   10                  15

Ile Gly Gln Ala Ile Ala Leu Glu Leu Gly Arg Gln Gly Ala Thr Val
                20                  25                  30

Ile Gly Thr Ala Thr Ser Ala Ser Gly Ala Glu Arg Ile Ala Ala Thr
            35                  40                  45

Leu Lys Glu His Gly Ile Thr Gly Thr Gly Met Glu Leu Asn Val Thr
```

```
            50                  55                  60
Ser Ala Glu Ser Val Glu Ala Val Leu Ala Ala Ile Gly Glu Gln Phe
 65                  70                  75                  80

Gly Ala Pro Ala Ile Leu Val Asn Asn Ala Gly Ile Thr Arg Asp Asn
                     85                  90                  95

Leu Met Leu Arg Met Lys Asp Asp Glu Trp Phe Asp Val Ile Asp Thr
                100                 105                 110

Asn Leu Asn Ser Leu Tyr Arg Leu Ser Lys Gly Val Leu Arg Gly Met
            115                 120                 125

Thr Lys Ala Arg Trp Gly Arg Ile Ile Ser Ile Gly Ser Val Val Gly
        130                 135                 140

Ala Met Gly Asn Ala Gly Gln Ala Asn Tyr Ala Ala Ala Lys Ala Gly
145                 150                 155                 160

Leu Glu Gly Phe Ser Arg Ala Leu Ala Arg Glu Val Gly Ser Arg Gly
                165                 170                 175

Ile Thr Val Asn Ser Val Thr Pro Gly Phe Ile Asp Thr Asp Met Thr
                180                 185                 190

Arg Glu Leu Pro Glu Ala Gln Arg Glu Ala Leu Gln Thr Gln Ile Pro
            195                 200                 205

Leu Gly Arg Leu Gly Gln Ala Asp Glu Ile Ala Lys Val Val Ser Phe
        210                 215                 220

Leu Ala Ser Asp Gly Ala Ala Tyr Val Thr Gly Ala Thr Val Pro Val
225                 230                 235                 240

Asn Gly Gly Met Tyr Met
                245

<210> SEQ ID NO 8
<211> LENGTH: 262
<212> TYPE: PRT
<213> ORGANISM: Enterococcus faecalis

<400> SEQUENCE: 8

Met Asp Leu Thr Asn Lys Val Val Val Thr Gly Gly Ser Ala Gly
 1               5                  10                  15

Leu Gly Glu Gln Ile Cys Tyr Glu Ala Ala Lys Gln Gly Ala Val Val
                 20                  25                  30

Val Val Cys Ala Arg Arg Ile Asn Leu Ile Gly Lys Val Arg Glu Gln
             35                  40                  45

Cys Ala Val Leu Ser Gly Arg Glu Ala Phe Ser Tyr Gln Leu Asp Ile
 50                  55                  60

Ala Asp Pro Glu Ser Val Arg Val Val Glu Ala Ile Ser Ala Glu
 65                  70                  75                  80

Val Gly Pro Ile Asp Val Leu Val Asn Asn Ala Gly Phe Gly Leu Phe
                 85                  90                  95

Glu Asn Phe Val Glu Ile Asp Leu Ala Val Ala Arg Gln Met Phe Asp
                100                 105                 110

Val Asn Val Leu Gly Met Met Thr Phe Thr Gln Lys Val Ala Ile Lys
            115                 120                 125

Met Ile Glu Ala Gly Gln Gly His Ile Ile Asn Val Ala Ser Met Ala
        130                 135                 140

Gly Lys Met Ala Thr Ala Lys Ser Thr Val Tyr Ser Ala Thr Lys Phe
145                 150                 155                 160

Ala Val Leu Gly Phe Ser Asn Ala Leu Arg Leu Glu Leu Lys Pro Leu
                165                 170                 175
```

```
Gly Val Ala Val Thr Thr Val Asn Pro Gly Pro Ile Gln Thr Glu Phe
                180                 185                 190

Phe Asp Lys Ala Asp Pro Thr Gly Thr Tyr Leu Ala Ala Val Asp Lys
            195                 200                 205

Ile Val Leu Asp Pro Thr Lys Leu Ala Lys Glu Val Val Gly Ser Met
210                 215                 220

Gly Thr Ser Arg Arg Glu Ile Asn Arg Pro Phe Val Met Glu Ala Ala
225                 230                 235                 240

Ala Arg Phe Tyr Thr Leu Phe Pro His Leu Gly Asp Phe Ile Ala Gly
            245                 250                 255

Asn Ile Leu Asn Lys Lys
            260
```

<210> SEQ ID NO 9
<211> LENGTH: 319
<212> TYPE: PRT
<213> ORGANISM: Pseudomonas syringae

<400> SEQUENCE: 9

```
Met Arg Arg Ile Leu Ile Thr Gly Ala Asn Gly Phe Val Gly Gln Ile
1               5                   10                  15

Leu Cys Ser Met Leu Arg Gln Ala Gly His His Val Ile Ala Leu Val
            20                  25                  30

Gly Ala Glu Ser Ala Leu Ser Ser His Ala Asp Glu Ser Val Arg Cys
        35                  40                  45

Asp Ile Arg Asp Ala Ser Gly Leu Glu Gln Ala Leu Cys Arg Ala Ala
    50                  55                  60

Pro Thr His Val Val His Leu Ala Ala Ile Thr His Val Pro Thr Ser
65                  70                  75                  80

Phe Asn Asn Pro Val Leu Thr Trp Gln Thr Asn Val Met Gly Ser Val
                85                  90                  95

Asn Leu Leu Gln Ala Leu Gln Arg Ser Ala Pro Glu Ala Phe Val Leu
            100                 105                 110

Phe Val Ser Ser Ser Glu Val Tyr Gly Glu Thr Phe Lys Gln Gly Thr
        115                 120                 125

Ala Leu Gly Glu Asp Ser Ala Cys Lys Pro Met Asn Pro Tyr Ala Ala
130                 135                 140

Ser Lys Leu Ala Ala Glu Ala Ala Phe Asn Glu Tyr Phe Arg Gln Gly
145                 150                 155                 160

Arg Lys Gly Ile Val Val Arg Pro Phe Asn His Ile Gly Ala Arg Gln
                165                 170                 175

Ser Pro Asp Phe Ala Thr Ala Ser Phe Ala Arg Gln Ile Ala Leu Ile
            180                 185                 190

Glu Ala Gly Lys Gln Ala Pro Gln Leu Lys Val Gly Asn Leu Gln Ala
        195                 200                 205

Ala Arg Asp Phe Leu Asp Val His Asp Val Cys Asp Ala Tyr Val Ala
210                 215                 220

Leu Leu Gln Leu Ala Asp Glu Gln Glu Arg Tyr Pro Gly Cys Leu Asn
225                 230                 235                 240

Ile Cys Arg Gly Glu Pro Thr Ser Leu Gln Thr Leu Leu Thr Gln Leu
                245                 250                 255

Met Ala Leu Ser Ser Ser Val Ile Glu Val Thr Ile Asp Pro Asp Arg
            260                 265                 270

Met Arg Pro Ser Asp Ile Pro Ser Ala Phe Gly Asn Asn Ser Ala Met
        275                 280                 285
```

```
Arg Cys Ala Thr Gly Trp Lys Pro Lys Thr Leu Asp Asp Thr Leu
        290                 295                 300

Glu Ala Leu Leu Asn Tyr Trp Arg His Glu Val Ile Ser Ala Val
305                 310                 315
```

<210> SEQ ID NO 10
<211> LENGTH: 368
<212> TYPE: PRT
<213> ORGANISM: Pseudomonas cannabina

<400> SEQUENCE: 10

```
Met Ser Leu Leu Leu Glu Pro Tyr Thr Leu Arg Gln Leu Thr Leu Arg
1               5                   10                  15

Asn Arg Ile Ala Val Ser Pro Met Cys Gln Tyr Ser Ser Val Asp Gly
            20                  25                  30

Leu Ala Asn Asp Trp His Leu His Leu Gly Ser Arg Ala Val Gly
        35                  40                  45

Gly Ala Gly Leu Val Ile Ser Glu Ala Met Ala Val Thr Pro Asp Gly
50                  55                  60

Arg Ile Thr Pro Glu Asp Leu Gly Leu Trp Asn Asp Glu Gln Ile Glu
65                  70                  75                  80

Pro Leu Gln Arg Ile Thr Arg Phe Ile Asn Thr Gln Gly Ala Val Ala
                85                  90                  95

Gly Ile Gln Leu Ala His Ala Gly Arg Lys Ala Ser Thr Trp Arg Pro
            100                 105                 110

Trp Leu Gly Lys His Gly Ser Val Pro Leu Thr Glu Gly Gly Trp Thr
        115                 120                 125

Pro Val Gly Pro Ser Ala Ile Ala Phe Asp Pro Gln His Thr Ala Pro
130                 135                 140

Leu Gln Leu Ser Glu Thr Gln Ile Gln Glu Leu Ile Lys Ala Phe Val
145                 150                 155                 160

Asp Ser Ala Arg Arg Ala Leu Thr Ala Gly Phe Lys Val Val Glu Ile
                165                 170                 175

His Ala Ala His Gly Tyr Leu Leu His Gln Phe Leu Ser Pro Leu Ser
            180                 185                 190

Asn Gln Arg Thr Asp Gln Tyr Gly Gly Ser Phe Glu Asn Arg Ile Arg
        195                 200                 205

Leu Thr Leu Gln Val Thr Glu Ala Val Arg Ala Val Trp Pro Gln Glu
210                 215                 220

Leu Pro Leu Phe Val Arg Val Ser Ala Thr Asp Trp Val Glu Asp Gly
225                 230                 235                 240

Trp Asn Ala Glu Glu Thr Val Glu Leu Ala Arg Arg Leu Lys Ala Leu
                245                 250                 255

Gly Thr Asp Leu Ile Asp Val Ser Ser Gly Gly Thr Ser Ala Asn Ala
            260                 265                 270

Glu Ile Pro Val Gly Pro Gly Tyr Gln Thr Arg Phe Ala Glu Gln Val
        275                 280                 285

Arg Lys Glu Ala Asp Ile Ala Thr Gly Thr Val Gly Met Ile Thr Asp
290                 295                 300

Pro Ala Gln Ala Glu His Ile Leu Arg Thr Gly Gln Ala Asp Ile Ile
305                 310                 315                 320

Leu Leu Ala Arg Glu Leu Leu Arg Asp Pro Tyr Trp Pro Leu Arg Ala
                325                 330                 335

Asp Glu Asp Leu Gly Gly Arg Gln Ala Thr Trp Pro Ala Gln Tyr Gln
```

340                 345                 350
Arg Ala Thr His Arg Asp Gln Pro Ile His Glu Ser Asp Leu Arg Asp
            355                 360                 365

<210> SEQ ID NO 11
<211> LENGTH: 344
<212> TYPE: PRT
<213> ORGANISM: Saccharomyces cerevisiae

<400> SEQUENCE: 11

Met Ser Ser Ser Leu Arg Val Leu Ala Ile Gly Asn Asn Pro Asn
1               5                   10                  15

Ile Leu Phe Tyr Thr Ser Arg Phe Gln Leu Ala Lys Asn Ile Asp Leu
                20                  25                  30

Tyr His Val Asn Asp Ser Lys Ser Cys Gln Phe Glu Ile Glu Thr Glu
            35                  40                  45

Tyr Tyr Gly Lys Asp Arg Phe Glu Leu Glu Asn His Phe Thr Ser Ile
        50                  55                  60

Glu His Leu Thr Glu Ala Leu Ser Ser Lys Ser Ser Glu Ala Val Phe
65                  70                  75                  80

Asp Ile Ile Ile Met Ser Ala Pro Ser Leu Gln Glu Leu Ser Ser Leu
                85                  90                  95

Ala Ser Lys Leu Thr Ser Ile Ile Asp Ser Asn Thr Lys Ile Phe Leu
            100                 105                 110

Glu Ser Ser Gly Phe Ile Gln Leu Glu Pro Phe Val Lys Leu Ser Met
        115                 120                 125

Glu Ser Pro His Val Asn Val Phe Ser Ile Leu Thr Asp Leu Asp Ile
130                 135                 140

Arg Gln Ile Gly Pro Asn His Phe Lys His Phe Pro Ser Thr Ala Lys
145                 150                 155                 160

Glu Asn Thr Ile Tyr Leu Gly Glu Ser Lys Ser Ser Thr Glu Lys Tyr
                165                 170                 175

Ser Ser Gly Val Ile Thr Leu Leu Thr Thr Phe Glu Lys Leu Phe Ala
            180                 185                 190

Lys Leu Phe Ser Asn Ile Lys Ile Asn Leu Cys Asn Phe Ser Ser Ile
        195                 200                 205

Glu Phe Leu Ser Gln Gln Trp Lys Leu Ala Ile Ser Arg Ile Cys Phe
210                 215                 220

Asp Pro Leu Leu Ile Met Phe Glu Gln Glu Asn Pro Ser Asp Leu Asp
225                 230                 235                 240

Gln Gln Ile Ile Ala Lys Pro Leu Ile Ser Gly Leu Val Thr Glu Ile
                245                 250                 255

Ile Thr Val Ala Lys Thr Met Gly Ala Arg Leu Asn Ser Ser His Asp
            260                 265                 270

Asn Glu Asn Ser Leu Leu Ser Leu Trp Lys Asn Ser Tyr His Ser Thr
        275                 280                 285

Asn Lys Pro Pro Ala Leu Val Tyr His Phe Ile His Gln Thr Thr Pro
290                 295                 300

Leu Asn Ile Asp Ile Leu Leu Leu Gln Thr Ile Leu Leu Ala Asp Asp
305                 310                 315                 320

Phe Gly Ile Lys Thr Pro Tyr Leu Glu Phe Leu Tyr Ser Val Leu Ser
                325                 330                 335

Gln Phe Glu Arg Leu Asn Ser Gly
            340

<210> SEQ ID NO 12
<211> LENGTH: 319
<212> TYPE: PRT
<213> ORGANISM: Thermotoga maritima

<400> SEQUENCE: 12

```
Met Glu Tyr Arg Lys Val Gly Lys Trp Gly Val Lys Ile Ser Glu Leu
1               5                   10                  15

Ser Leu Gly Ser Trp Leu Thr Phe Gly Lys Gln Leu Asp Leu Asp Thr
            20                  25                  30

Ala Thr Glu Val Val Lys Lys Ala Phe Asn Ser Gly Ile Asn Phe Phe
        35                  40                  45

Asp Thr Ala Glu Ala Tyr Ala Gly Gly Ile Ala Glu Ala Met Leu Gly
    50                  55                  60

Lys Ile Leu Lys Asn Phe Arg Arg Glu Asp Leu Val Val Ser Thr Lys
65                  70                  75                  80

Ile Phe Trp Gly Gly Ser Gly Pro Asn Asp Leu Gly Leu Ser Lys Lys
                85                  90                  95

His Leu Glu Gly Thr Trp Asn Ser Leu Lys Arg Leu Gln Met Asp
            100                 105                 110

Tyr Val Asp Ile Leu Tyr Cys His Arg Pro Asp Pro Asn Val Pro Met
            115                 120                 125

Glu Glu Val Val Phe Ala Met Asp Tyr Ile Leu Arg Glu Gly Leu Ala
    130                 135                 140

Leu Tyr Trp Gly Thr Ser Glu Trp Ser Ala Lys Glu Ile Glu Glu Ala
145                 150                 155                 160

His Arg Val Cys Lys Glu Leu Gly Val Met Pro Pro Ile Val Glu Gln
                165                 170                 175

Pro Gln Tyr Asn Met Phe Val Arg Glu Arg Val Glu Lys Glu Tyr Ala
            180                 185                 190

Pro Leu Tyr Glu Lys Tyr Gly Met Gly Leu Thr Thr Tyr Ser Pro Leu
        195                 200                 205

Ala Ser Gly Leu Leu Ser Gly Lys Tyr Asn Asn Gly Ile Pro Glu Gly
    210                 215                 220

Ser Arg Leu Ala Thr Phe Pro Gln Val Arg Lys Trp Leu Glu Glu Gly
225                 230                 235                 240

Gly Leu Leu Asn Glu Lys Thr Phe Lys Lys Leu Arg Lys Leu Gln Asn
                245                 250                 255

Ile Ala Asp Gln Leu Gly Ala Ser Leu Pro Gln Leu Ala Ile Ala Trp
            260                 265                 270

Ile Leu Lys Asn Lys Asn Val Ser Ser Val Ile Leu Gly Val Ser Arg
        275                 280                 285

Pro Glu Gln Leu Glu Glu Asn Leu Lys Ala Val Glu Ile Lys Glu Lys
    290                 295                 300

Leu Thr Glu Asp Val Met Glu Glu Ile Glu Lys Ile Leu Asn Glu
305                 310                 315
```

<210> SEQ ID NO 13
<211> LENGTH: 326
<212> TYPE: PRT
<213> ORGANISM: Agrobacterium fabrum

<400> SEQUENCE: 13

```
Met Thr Leu Ala Asn Leu Pro Pro Leu Val Thr Val Phe Gly Gly Ser
1               5                   10                  15
```

```
Gly Phe Val Gly Arg His Val Val Arg Met Leu Ala Lys Arg Gly Tyr
            20                  25                  30

Arg Ile Arg Val Ala Val Arg Arg Pro Asp Leu Ala Gly Phe Leu Gln
        35                  40                  45

Pro Leu Gly Asn Val Gly Gln Ile Ser Phe Ala Gln Ala Asn Leu Arg
    50                  55                  60

Tyr Arg Asp Ser Ile Ile Lys Ala Val Glu Asp Ala Asp His Val Val
65                  70                  75                  80

Asn Cys Val Gly Ile Leu Ala Glu Ser Gly Arg Asn Thr Phe Asp Ala
                85                  90                  95

Val Gln Glu Phe Gly Ala Lys Ala Ile Ala Glu Ala Ala Arg Asp Thr
            100                 105                 110

Gly Ala Thr Leu Thr His Ile Ser Ala Ile Gly Ala Asp Ala Asn Ser
        115                 120                 125

Gln Thr Gly Tyr Gly Arg Thr Lys Gly Arg Ala Glu Ala Ala Ile His
    130                 135                 140

Ser Val Leu Pro Gly Ala Val Ile Leu Arg Pro Ser Ile Ile Phe Gly
145                 150                 155                 160

Pro Glu Asp Asp Phe Phe Asn Lys Phe Ala Lys Met Ala Arg Asn Leu
                165                 170                 175

Pro Phe Leu Pro Leu Ile Gly Gly Lys Thr Lys Phe Gln Pro Val
            180                 185                 190

Tyr Val Glu Asp Val Ala Glu Ala Val Ala Arg Ser Val Asp Gly Lys
        195                 200                 205

Leu Lys Pro Gly Ala Ile Tyr Glu Leu Gly Pro Asp Val Met Thr
    210                 215                 220

Phe Arg Asp Cys Leu Glu Ala Val Leu Ala Ala Thr Tyr Arg Glu Arg
225                 230                 235                 240

Ser Phe Val Asn Leu Pro Phe Gly Val Ala Ser Met Ile Gly Lys Leu
                245                 250                 255

Ala Ser Leu Val Pro Leu Ile Thr Pro Pro Leu Thr Pro Asp Gln Val
            260                 265                 270

Thr Met Leu Lys Lys Asp Asn Val Val Ser Ala Glu Ala Glu Lys Lys
        275                 280                 285

Gly Leu Thr Leu Glu Gly Ile Gly Ile Thr Pro Val Arg Val Ala Ser
    290                 295                 300

Val Leu Pro Ser Tyr Met Val Gln Tyr Arg Gln His Gly Gln Phe Ser
305                 310                 315                 320

Asn Ala Gly Lys Ala Ala
            325

<210> SEQ ID NO 14
<211> LENGTH: 311
<212> TYPE: PRT
<213> ORGANISM: Rhizobium meliloti

<400> SEQUENCE: 14

Met Thr Ala Glu Val Phe Asp Pro Arg Ala Leu Arg Asp Ala Phe Gly
1               5                   10                  15

Ala Phe Ala Thr Gly Val Thr Val Thr Ala Ser Asp Ala Ala Gly
            20                  25                  30

Lys Pro Ile Gly Phe Thr Ala Asn Ser Phe Thr Ser Val Ser Leu Asp
        35                  40                  45

Pro Pro Leu Leu Leu Val Cys Leu Ala Lys Ser Ser Arg Asn Tyr Glu
    50                  55                  60
```

Ser Met Thr Ser Ala Gly Arg Phe Ala Ile Asn Val Leu Ser Glu Thr
65                  70                  75                  80

Gln Lys Asp Val Ser Asn Thr Phe Ala Arg Pro Val Glu Asp Arg Phe
            85                  90                  95

Ala Ala Val Asp Trp Arg Leu Gly Arg Asp Gly Cys Pro Ile Phe Ser
        100                 105                 110

Asp Val Ala Ala Trp Phe Glu Cys Ser Met Gln Asp Ile Ile Glu Ala
    115                 120                 125

Gly Asp His Val Ile Ile Ile Gly Arg Val Thr Ala Phe Glu Asn Ser
130                 135                 140

Gly Leu Asn Gly Leu Gly Tyr Ala Arg Gly Gly Tyr Phe Thr Pro Arg
145                 150                 155                 160

Leu Ala Gly Lys Ala Val Ser Ala Ala Val Glu Gly Glu Ile Arg Leu
                165                 170                 175

Gly Ala Val Leu Glu Gln Gln Gly Ala Val Phe Leu Ala Gly Asn Glu
            180                 185                 190

Thr Leu Ser Leu Pro Asn Cys Thr Val Glu Gly Gly Asp Pro Ala Arg
        195                 200                 205

Thr Leu Ala Ala Tyr Leu Glu Gln Leu Thr Gly Leu Asn Val Thr Ile
    210                 215                 220

Gly Phe Leu Tyr Ser Val Tyr Glu Asp Lys Ser Asp Gly Arg Gln Asn
225                 230                 235                 240

Ile Val Tyr His Ala Leu Ala Ser Asp Gly Ala Pro Arg Gln Gly Arg
                245                 250                 255

Phe Leu Arg Pro Ala Glu Leu Ala Ala Lys Phe Ser Ser Ser Ala
            260                 265                 270

Thr Ala Asp Ile Ile Asn Arg Phe Val Leu Glu Ser Ser Ile Gly Asn
        275                 280                 285

Phe Gly Ile Tyr Phe Gly Asp Glu Thr Gly Thr Val His Pro Ile
    290                 295                 300

Ala Asn Lys Asp Ala His Ser
305                 310

<210> SEQ ID NO 15
<211> LENGTH: 240
<212> TYPE: PRT
<213> ORGANISM: Lactobacillus paraplantarum

<400> SEQUENCE: 15

Met Asp Glu Val Ile Leu Val Thr Gly Ala Ala Lys Gly Ile Gly Leu
1               5                   10                  15

Ala Thr Val Lys Arg Leu Ser Ser Gln Gly Ala Arg Val Ile Leu Asn
            20                  25                  30

Val His His Glu Ile Glu Ala Thr Asp Trp Gln Ala Leu Thr Ala Glu
        35                  40                  45

Tyr Pro Arg Leu Thr Gln Leu Val Gly Asp Val Ser Asp Asp Gln Ser
    50                  55                  60

Ala Ala Asn Leu Ile Asp Thr Val Met Thr Asn Phe Gly Arg Leu Asp
65                  70                  75                  80

Gly Leu Val Asn Asn Ala Gly Val Thr His Asp Gln Leu Leu Thr Arg
                85                  90                  95

Leu His Ala Glu Asp Phe Met Ser Val Ile Gln Thr Asn Leu Leu Gly
            100                 105                 110

Thr Phe Asn Met Thr Lys Tyr Ala Leu Lys Val Met Gln Arg Gln Arg

```
            115                 120                 125
Gln Gly Ala Ile Val Asn Val Ala Ser Val Val Gly Leu His Gly Asn
    130                 135                 140
Val Gly Gln Ala Asn Tyr Ala Ala Ser Lys Ala Gly Ile Ile Gly Leu
145                 150                 155                 160
Thr Lys Thr Thr Ala Lys Glu Ala Ala Arg Gln Val Arg Cys Asn
                165                 170                 175
Ala Val Ala Pro Gly Met Ile Thr Thr Ala Met Thr Ala Gln Leu Asn
            180                 185                 190
Asp Arg Val Thr Ala Ala Leu Ser Asp Ile Pro Leu Lys Arg Phe
            195                 200                 205
Gly Thr Pro Asp Glu Ile Ala Gln Ala Ile Asp Phe Leu Leu His Gln
            210                 215                 220
Pro Tyr Leu Thr Gly Gln Val Leu Thr Val Asp Gly Gly Met Thr Ile
225                 230                 235                 240
```

<210> SEQ ID NO 16
<211> LENGTH: 340
<212> TYPE: PRT
<213> ORGANISM: Botryontinia fuckeliana

<400> SEQUENCE: 16

```
Met Arg Val Leu Leu Thr Gly Gly Ser Gly Phe Ile Ala Ala His Ile
1               5                   10                  15
Leu Asp Ile Leu Leu Ser Arg Gly His Thr Val Ile Thr Thr Val Arg
            20                  25                  30
Ser Gln Gln Lys Ile Asp Ala Ile Lys Ala Ala His Pro Asp Val Pro
        35                  40                  45
Ala Ser Lys Leu Asp Phe Phe Ile Val Glu Asp Ile Ala Lys Glu Asn
    50                  55                  60
Ala Phe Asp Glu Cys Leu Lys Lys Phe Gly Glu Gly Leu Glu Ala Val
65                  70                  75                  80
Leu His Thr Ala Ser Pro Phe His Phe Asn Val Thr Asp Thr Lys Lys
                85                  90                  95
Asp Leu Leu Asp Pro Ala Ile Ile Gly Thr Thr Ala Ile Leu His Ala
            100                 105                 110
Ile Lys Lys Phe Ala Pro Ser Val Thr Arg Val Val Thr Ser Ser
        115                 120                 125
Phe Ala Ser Ile Ile Asp Ala Ser Lys Gly Asn Trp Pro Asp His Thr
130                 135                 140
Tyr Thr Glu Glu Asp Trp Asn Pro Ile Thr Leu Ser Glu Ala Val Glu
145                 150                 155                 160
Asn Pro Ser Asn Gly Tyr Arg Ala Ser Lys Thr Phe Ala Glu Lys Ala
                165                 170                 175
Ala Trp Glu Phe Val Glu Lys Glu Asn Pro Asn Phe Thr Leu Ser Thr
            180                 185                 190
Met Asn Pro Pro Leu Val Leu Gly Pro Ile Val His Tyr Leu Asn Ser
            195                 200                 205
Leu Asp Ala Leu Asn Thr Ser Asn Gln Arg Val Arg Asp Val Leu Gln
            210                 215                 220
Gly Lys Trp Lys Glu Glu Ile Pro Gly Thr Gly Thr Phe Ile Trp Ile
225                 230                 235                 240
Asp Val Arg Asp Leu Ala Leu Ala His Val Lys Ala Ile Glu Ile Ala
                245                 250                 255
```

```
Glu Ala Ala Gly Lys Arg Phe Phe Ile Thr Glu Gly Tyr Phe Ser Asn
            260                 265                 270

Lys Glu Ile Cys Glu Ile Ile Arg Lys Asn Phe Pro Glu Asp Gly Gly
        275                 280                 285

Glu Leu Pro Gly Lys Glu Val Lys Gly Gly Tyr Pro Glu Gly Gly
    290                 295                 300

Ile Tyr Lys Phe Asp Asn Ala Arg Thr Arg Ser Val Leu Gly Leu Glu
305                 310                 315                 320

Phe Arg Gly Leu Glu Ser Ile Val Asp Leu Val Lys Ser Leu Lys
                325                 330                 335

Glu Val Gly Val
            340

<210> SEQ ID NO 17
<211> LENGTH: 243
<212> TYPE: PRT
<213> ORGANISM: Fusarium oxysporum

<400> SEQUENCE: 17

Met Ser Arg Asn Leu Ala Leu Val Thr Gly Ser Thr Gln Gly Ile Gly
1               5                   10                  15

Leu Ala Val Ala Lys Glu Leu Ala Ile Lys His Asn Tyr Gln Val Leu
            20                  25                  30

Leu Gly Val Arg Asn Thr Lys Ala Gly Glu Glu Ile Ala Ser Asp Leu
        35                  40                  45

Arg Lys Glu Gly His Glu Ala Ser Val Val Glu Leu Asp Leu Thr Ser
    50                  55                  60

Ala Asp Ser Ile Asp Lys Ala Val Lys His Ile Asp Glu Lys Tyr Gly
65                  70                  75                  80

Tyr Leu Asp Val Leu Ile Asn Asn Ala Gly Val Leu Leu Asp Arg Gln
                85                  90                  95

Glu Gly Leu Ser Thr Trp Asp Leu Phe Ser Lys Thr Phe Thr Thr Asn
            100                 105                 110

Val Phe Gly Thr Gly Cys Leu Thr Gln Ser Leu Leu Pro Leu Leu Arg
        115                 120                 125

Lys Ala Lys Asn Ser Pro Pro Arg Ile Val Phe Val Thr Ser Val Met
    130                 135                 140

Gly Ser Leu Thr Lys Ala Thr Asp Glu Thr Thr Thr Tyr Tyr Asn Ile
145                 150                 155                 160

Asp Tyr Lys Ala Tyr Asp Ala Ser Lys Ala Ala Val Asn Met Leu Met
                165                 170                 175

Phe Asn Phe Ala Arg Glu Leu Asp Ala Val Gly Gly Lys Val Asn Ser
            180                 185                 190

Val Cys Pro Gly Leu Val Lys Thr Gly Leu Thr Asn Tyr His Glu Trp
        195                 200                 205

Gly Thr Ser Pro Glu Thr Gly Ala Glu Arg Ile Val Glu Met Ala Thr
    210                 215                 220

Ile Gly Glu Asp Gly Pro Thr Lys Thr Ile Ser Asp Arg Asn Gly Glu
225                 230                 235                 240

Leu Pro Leu

<210> SEQ ID NO 18
<211> LENGTH: 240
<212> TYPE: PRT
<213> ORGANISM: Lactobacillus delbrueckii
```

<400> SEQUENCE: 18

| Met | Asp | Leu | Gln | Asn | Lys | Arg | Val | Leu | Val | Thr | Gly | Ser | Thr | Gln | Gly |
|---|---|---|---|---|---|---|---|---|---|---|---|---|---|---|---|
| 1 | | | | 5 | | | | | 10 | | | | | 15 | |

| Ile | Gly | Ala | Ala | Thr | Ala | Leu | Ala | Phe | Ala | Gln | Lys | Gly | Cys | Gln | Val |
|---|---|---|---|---|---|---|---|---|---|---|---|---|---|---|---|
| | | | 20 | | | | 25 | | | | | 30 | | | |

| Leu | Leu | Asn | Gly | Arg | Arg | Pro | Glu | Leu | Pro | Glu | Glu | Ile | Ala | Asp | Gln |
|---|---|---|---|---|---|---|---|---|---|---|---|---|---|---|---|
| | | 35 | | | | | 40 | | | | | 45 | | | |

| Leu | Glu | Lys | Ile | Gly | Ala | Asp | Tyr | Gln | Tyr | Phe | Ser | Ala | Asp | Val | Ser |
|---|---|---|---|---|---|---|---|---|---|---|---|---|---|---|---|
| | 50 | | | | | 55 | | | | | 60 | | | | |

| Asp | Glu | Gly | Ala | Ile | Lys | Gln | Leu | Phe | Lys | Glu | Ile | Gly | Glu | Ile | Asp |
|---|---|---|---|---|---|---|---|---|---|---|---|---|---|---|---|
| 65 | | | | | 70 | | | | | 75 | | | | | 80 |

| Ile | Leu | Val | Asn | Asn | Ala | Gly | Ile | Thr | Lys | Asp | Gln | Ile | Met | Ile | Gly |
|---|---|---|---|---|---|---|---|---|---|---|---|---|---|---|---|
| | | | | 85 | | | | | 90 | | | | | 95 | |

| Met | Lys | Leu | Ala | Asp | Phe | Asp | Gln | Val | Ile | Lys | Val | Asn | Leu | Arg | Ser |
|---|---|---|---|---|---|---|---|---|---|---|---|---|---|---|---|
| | | | 100 | | | | 105 | | | | | 110 | | | |

| Ser | Phe | Met | Leu | Thr | Gln | Lys | Ala | Leu | Lys | Lys | Met | Leu | Lys | Lys | Arg |
|---|---|---|---|---|---|---|---|---|---|---|---|---|---|---|---|
| | | | 115 | | | | 120 | | | | | 125 | | | |

| Ser | Gly | Ala | Ile | Ile | Asn | Met | Ala | Ser | Ile | Val | Gly | Gln | His | Gly | Asn |
|---|---|---|---|---|---|---|---|---|---|---|---|---|---|---|---|
| | 130 | | | | | 135 | | | | | 140 | | | | |

| Ala | Gly | Gln | Ala | Asn | Tyr | Ala | Ala | Ser | Lys | Ala | Gly | Val | Ile | Ala | Leu |
|---|---|---|---|---|---|---|---|---|---|---|---|---|---|---|---|
| 145 | | | | | 150 | | | | | 155 | | | | | 160 |

| Thr | Gln | Thr | Ala | Ala | Lys | Glu | Ala | Ala | Gly | Arg | Gly | Val | Arg | Val | Asn |
|---|---|---|---|---|---|---|---|---|---|---|---|---|---|---|---|
| | | | | 165 | | | | | 170 | | | | | 175 | |

| Ala | Ile | Ala | Pro | Gly | Met | Ile | Ala | Ser | Gln | Met | Thr | Ala | Val | Leu | Pro |
|---|---|---|---|---|---|---|---|---|---|---|---|---|---|---|---|
| | | | 180 | | | | 185 | | | | | 190 | | | |

| Asp | Glu | Val | Lys | Glu | Gln | Ala | Leu | Ser | Gln | Ile | Pro | Leu | Ala | Arg | Phe |
|---|---|---|---|---|---|---|---|---|---|---|---|---|---|---|---|
| | 195 | | | | | 200 | | | | | 205 | | | | |

| Gly | Lys | Ala | Glu | Glu | Val | Ala | Gln | Ala | Ala | Val | Phe | Leu | Ala | Glu | Asn |
|---|---|---|---|---|---|---|---|---|---|---|---|---|---|---|---|
| | | 210 | | | | | 215 | | | | | 220 | | | |

| Asp | Tyr | Val | Thr | Gly | Gln | Thr | Leu | Val | Val | Asp | Gly | Gly | Met | Thr | Ile |
|---|---|---|---|---|---|---|---|---|---|---|---|---|---|---|---|
| 225 | | | | | 230 | | | | | 235 | | | | | 240 |

<210> SEQ ID NO 19
<211> LENGTH: 338
<212> TYPE: PRT
<213> ORGANISM: Acremonium

<400> SEQUENCE: 19

| Met | Thr | Lys | Val | Leu | Val | Ala | Gly | Gly | Ser | Gly | Phe | Ile | Gly | Ala | His |
|---|---|---|---|---|---|---|---|---|---|---|---|---|---|---|---|
| 1 | | | | 5 | | | | | 10 | | | | | 15 | |

| Ile | Leu | Glu | Gln | Leu | Leu | Ala | Lys | Gly | His | Ser | Val | Val | Thr | Thr | Val |
|---|---|---|---|---|---|---|---|---|---|---|---|---|---|---|---|
| | | | 20 | | | | 25 | | | | | 30 | | | |

| Arg | Ser | Lys | Glu | Lys | Ala | Gln | Lys | Ile | Leu | Asp | Ala | His | Lys | Ala | Glu |
|---|---|---|---|---|---|---|---|---|---|---|---|---|---|---|---|
| | | 35 | | | | | 40 | | | | | 45 | | | |

| Ala | Asp | Arg | Leu | Glu | Val | Ala | Ile | Val | Pro | Glu | Ile | Ala | Arg | Glu | Asp |
|---|---|---|---|---|---|---|---|---|---|---|---|---|---|---|---|
| | 50 | | | | | 55 | | | | | 60 | | | | |

| Ala | Phe | Asp | Glu | Val | Val | Lys | Thr | Pro | Gly | Ile | Glu | Val | Val | Ile | His |
|---|---|---|---|---|---|---|---|---|---|---|---|---|---|---|---|
| 65 | | | | | 70 | | | | | 75 | | | | | 80 |

| Pro | Ala | Ser | Pro | Cys | His | Leu | Asn | Phe | Thr | Asp | Pro | Gln | Lys | Glu | Leu |
|---|---|---|---|---|---|---|---|---|---|---|---|---|---|---|---|
| | | | | 85 | | | | | 90 | | | | | 95 | |

| Ile | Asp | Pro | Ala | Val | Leu | Gly | Thr | Thr | Asn | Ile | Leu | Arg | Ala | Ile | Lys |
|---|---|---|---|---|---|---|---|---|---|---|---|---|---|---|---|
| | | | 100 | | | | 105 | | | | | 110 | | | |

| Arg | Asp | Ala | Pro | Gln | Val | Arg | Arg | Val | Ile | Ile | Thr | Ser | Ser | Val | Ala |
|---|---|---|---|---|---|---|---|---|---|---|---|---|---|---|---|
| | | | 115 | | | | 120 | | | | | 125 | | | |

-continued

```
Ala Ile Phe Asn Thr Lys Asp Pro Val Ser Thr Leu Thr Glu Gln Ser
    130                 135                 140

Trp Asn Pro Asn Asp Leu Ser Asn Ile His Asp Ser Arg Ala Val Ala
145                 150                 155                 160

Tyr Cys Val Ser Lys Thr Leu Ala Glu Arg Ala Ala Trp Asp Tyr Val
                165                 170                 175

Asp Gln Glu Lys Pro Asn Phe Asp Leu Val Thr Val Asn Pro Pro Leu
            180                 185                 190

Val Leu Gly Pro Val Val Gly His Phe Ser Asn Val Asp Ser Ile Asn
        195                 200                 205

Ala Ser Asn Glu Cys Leu Ala Asn Leu Val Arg Gly Lys Trp Arg Asp
    210                 215                 220

Glu Ile Pro Pro Thr Gly Pro Val Asn Ile Trp Ile Asp Val Arg Asp
225                 230                 235                 240

Val Ala Ala Ala His Val Arg Ala Met Glu Arg Gln Glu Ala Gly Gly
                245                 250                 255

Lys Arg Leu Phe Thr Val Gly Gly Arg Phe Ser Tyr Thr Lys Ile Ala
            260                 265                 270

Glu Ile Val Arg Glu His Gly Pro Asp Arg Phe Lys Asp Lys Met Pro
        275                 280                 285

Arg Ala Glu Ala Arg Ser Gly Asp Ala Asn Tyr Thr Gly Pro Val Leu
    290                 295                 300

Lys Phe Asp Asn Gly Glu Thr Asn Arg Ile Leu Gly Ile Glu Trp Thr
305                 310                 315                 320

Pro Leu Glu Lys Ser Val Leu Asp Phe Val Glu Ser Ile Lys Glu Phe
                325                 330                 335

Asp Leu

<210> SEQ ID NO 20
<211> LENGTH: 348
<212> TYPE: PRT
<213> ORGANISM: Tricoderma

<400> SEQUENCE: 20

Met Thr Lys Val Leu Leu Thr Gly Gly Ser Gly Phe Ile Ala Ala His
1               5                   10                  15

Ile Leu Glu Gln Leu Leu Ala Lys Asn Tyr Thr Val Ile Thr Thr Val
                20                  25                  30

Arg Thr Lys Ser Lys Ala Asp Leu Ile Lys Glu Ala His Ala Asp Leu
            35                  40                  45

Val Lys Ser Gly Arg Leu Ser Val Ala Ile Val Pro Asp Ile Ala Val
        50                  55                  60

Leu Ser Ala Phe Asp Asp Leu Val Ala Lys Ile Ala Ser Gly Pro Asp
65                  70                  75                  80

Gly Asp Leu Glu Tyr Val Val His Thr Ala Ser Pro Leu Phe Phe Thr
                85                  90                  95

Phe Thr Asp Ala Gln Lys Glu Ile Ile Thr Pro Ala Leu Asn Gly Thr
            100                 105                 110

Arg Gly Ile Leu Glu Ala Val Lys Arg Ser Ala Pro Lys Val Lys Arg
        115                 120                 125

Val Val Ile Thr Ser Ser Phe Ala Ala Ile Leu Ser Glu Asp Asp Phe
    130                 135                 140

Thr Asn Pro Asn Ala Thr Phe Ser Glu Ser Ser Trp Asn Pro Asp Thr
145                 150                 155                 160
```

-continued

Val Lys Asp Ala Asn Arg Ser Ile Ala Thr Gly Tyr His Val Ser Lys
            165                 170                 175

Val Glu Ser Glu Arg Leu Ala Trp Asp Phe Ile Lys Asn Glu Lys Pro
        180                 185                 190

Asn Phe Asp Leu Val Thr Val Asn Pro Pro Leu Val Leu Gly Pro Val
            195                 200                 205

Ala His Ser Leu Ala Ser Val Asp Ala Ile Asn Ala Ser Asn Glu Arg
        210                 215                 220

Ile Ala Asp Leu Leu Arg Gly Lys Trp Lys Ala Glu Ile Pro Glu Thr
225                 230                 235                 240

Gly Ala Val Asp Leu Tyr Ile Asp Val Arg Asp Thr Ala Lys Ala His
            245                 250                 255

Ile Lys Ala Leu Glu Leu Pro Glu Ala Ser Gly His Arg Leu Phe Pro
        260                 265                 270

Val Ala Ser Arg Thr Ser Asn His Glu Ile Ala Lys Ile Ile Arg Asp
            275                 280                 285

Asn Phe Pro Glu Phe Ala Glu Arg Leu Pro Gly Pro Glu Val Lys Gly
        290                 295                 300

Gly Glu His Val Asp Glu Asn Lys Ala Tyr Lys Trp Asn Cys Asp Glu
305                 310                 315                 320

Thr Asn Lys Leu Leu Lys Ile Asp Trp Ile Pro Ile Glu Gln Ser Met
            325                 330                 335

Ile Asp Thr Val Asn Ser Leu Lys Asp Lys Gly Ile
            340                 345

<210> SEQ ID NO 21
<211> LENGTH: 302
<212> TYPE: PRT
<213> ORGANISM: Coprinopsis

<400> SEQUENCE: 21

Met Pro Thr Val Ser Pro Gly Ser Lys Val Leu Val Thr Gly Ala Asn
1               5                   10                  15

Gly Phe Ile Ala Ile Trp Val Val Arg Arg Leu Leu Glu Glu Gly Tyr
            20                  25                  30

Ser Val Arg Gly Thr Val Arg Ala Ala Ser Lys Ala Ser His Leu Lys
        35                  40                  45

Asp Ile Phe Lys Ser Tyr Gly Glu Lys Leu Glu Val Val Val Val Pro
    50                  55                  60

Asp Phe Thr Lys Glu Gly Ala Phe Asp Glu Leu Ile Lys Gly Met Asp
65                  70                  75                  80

Ala Ile Gln His Ile Ala Ser Pro Gly Pro Ala Asn Thr Asp Asp Leu
            85                  90                  95

Tyr Glu Ile Val Asn Pro Ala Val Asp Gly Thr Leu Asn Leu Leu Asn
            100                 105                 110

Thr Ala Leu Lys His Gly Ser Gly Leu Lys Arg Ile Val Ile Thr Ser
        115                 120                 125

Gly Ala Gly Ala Ile Ile Asp Thr Thr Thr Ala Trp Lys Phe Tyr Asn
    130                 135                 140

Asp His Lys Asn Val Ile Lys Trp Asp Leu Thr Val Leu Asn Pro Val
145                 150                 155                 160

Phe Val Phe Gly Pro Pro Ile His Glu Ile Gly Ala Ser Pro Met Thr
            165                 170                 175

Leu Asn Ser Ser Met Val His Phe Trp Val Asn Val Ile Ser Thr Asp
            180                 185                 190

```
Thr Pro Lys Thr Lys Glu Gly Leu Ser Phe Ala Ala Ser Trp Val Asp
            195                 200                 205

Val Arg Asp Val Ala Gln Gly His Val Leu Ala Leu Gln Lys Glu Ala
        210                 215                 220

Ala Gly Gly Glu Arg Ile Ile Leu Ser Glu Gly Ser Phe Val Trp Gln
225                 230                 235                 240

Asp Trp Val Asp Val Ala Asn Lys Phe Lys Ser Lys Arg Glu Leu Pro
                245                 250                 255

Lys Gly Met Pro Glu Ile Glu Arg Val Tyr Lys Phe Gln Met Asp Ala
            260                 265                 270

Ser Lys Ala Thr Arg Ile Leu Gly Ile Thr Tyr Arg Ser Lys Glu Asp
        275                 280                 285

Thr Met Lys Asp Leu Leu Glu Asp Phe Glu Arg Arg Gly Trp
            290                 295                 300

<210> SEQ ID NO 22
<211> LENGTH: 239
<212> TYPE: PRT
<213> ORGANISM: Exophiala

<400> SEQUENCE: 22

Met Lys Val Leu Leu Thr Gly Gly Ser Gly Phe Ile Ala Thr His Cys
1               5                   10                  15

Leu Asp Ala Leu Leu Lys His Gly His Glu Val Val Ile Thr Val Arg
            20                  25                  30

Ser Ala Glu Lys Gly Gln Ala Leu Val Asp Leu Phe Lys Gly Gln Lys
        35                  40                  45

Val Ser Tyr Thr Ile Val Lys Asp Ile Ser Val Pro Gly Ala Phe Asp
    50                  55                  60

Gln Ala Val Ile Ser Asp Pro Pro Phe Asp Ala Val Val His Thr Ala
65                  70                  75                  80

Ser Pro Phe His Tyr Asp Val Gln Asp Asn Lys Arg Asp Leu Leu Asp
                85                  90                  95

Pro Ala Ile Ile Gly Thr Thr Gly Ile Leu Glu Ser Ile Gln Lys Gly
            100                 105                 110

Ala Pro Ser Val Lys Lys Val Val Thr Ser Ser Phe Ala Ala Ile
        115                 120                 125

Ser Asn Pro Thr Ala Pro Lys Val Tyr Asp Glu Thr Val Trp Asn
    130                 135                 140

Gln Met Thr Met Glu Glu Ala Leu Thr Lys Asp Pro Gln Ala Val
145                 150                 155                 160

Tyr Arg Gly Ser Lys Thr Phe Ala Glu Lys Ala Ala Trp Glu Phe Val
                165                 170                 175

Glu Arg Glu Lys Pro Asn Phe Thr Leu Thr Val Leu Asn Pro Pro Val
            180                 185                 190

Ser His Phe Leu Phe Ser Arg His Lys Asp Val Ala Val Thr Phe Phe
        195                 200                 205

Ser Asp Ser Phe Gln His Cys Arg Trp Ser Thr Ala Arg Ser Cys Thr
    210                 215                 220

Pro Trp His His Trp Thr Ile Ser Thr Pro Arg Ala Ser Glu Ser
225                 230                 235
```

ENZYMATIC PROCESS FOR PRODUCTION OF MODIFIED HOP PRODUCTS

REFERENCE TO SEQUENCE LISTING, TABLE OR COMPUTER PROGRAM

The Sequence Listing concurrently submitted herewith under 37 C.F.R. § 1.821 in a computer readable form (CRF) via EFS-Web as file name KALSEC_76_US_DIV_Sequence_Listing_28_June_2021.txt is herein incorporated by reference. The electronic copy of the Sequence Listing was created on 28 Jun. 2021.

FIELD OF THE INVENTION

The present invention relates to a process for producing a beer bittering agent via enzyme catalyzed bioconversion of hop-derived isoalpha acids to dihydro-(rho)-isoalpha acids and to the novel enzyme catalysts which may be employed in such a process. Dihydro-(rho)-isoalpha acids have superior characteristics which improve utility as a beverage additive. Consumers may prefer dihydro-(rho)-isoalpha acids produced via this process, which does not require the use of harsh chemical reagents and which utilizes enzymes which may be naturally occurring.

BACKGROUND OF THE INVENTION

Traditional methods of bittering beer use whole fresh hops, whole dried hops, or hop pellets added during the kettle boil. Hop extracts made by extracting hops with supercritical carbon dioxide, or isomerized hop pellets, made by heating hops in the presence of a catalyst are more recent bittering innovations that have also been adopted by brewers. Hop pellets can also be added later in the brewing process and in the case of dry hopping, hops are added to the finished beer prior to filtration. These methods suffer from a poor utilization of the bittering compounds present in the hops, which impacts the cost unfavorably. Beer or other malt beverages produced in this manner are unstable to light and must be packaged in dark brown bottles or cans or placed to avoid the light induced formation of 3-methyl-2-butene-1-thiol (3-MBT) which gives a pronounced light-struck or skunky aroma. Placing bottles in cardboard boxes or completely wrapping them in light-proof or light-filtering paper, foil, or plastic coverings is another expensive method of protecting these beverages from light-struck flavor and aroma.

Bitterness in traditionally brewed beer is primarily derived from isoalpha acids. These compounds are formed during the brewing process by the isomerization of the humulones, which are naturally occurring compounds in the lupulin glands of the hop plant. A consequence of this is, given the natural instability of the isoalpha acids towards photochemical reactions in beer, a beverage prone to the formation of light-struck or skunky flavor and aroma.

Fully light stable beers or other malt beverages can be prepared using so-called advanced or modified hop acids. Beers made using these bittering agents can be packaged in non-colored flint glass bottles without fear of forming skunky aromas. Dihydro-(rho)-isoalpha acids are reduction products of isoalpha acids which are light stable. To date, these compounds have not been found in nature. Traditionally, the portion of the isoalpha acids which is responsible for the photochemistry has been altered by reduction of a carbonyl group using sodium borohydride.

Sodium borohydride is an inorganic compound that can be utilized for the reduction of ketones. It is extremely hazardous in case of skin contact, eye contact, inhalation, or ingestion, with an oral LD50 of 160 mg/kg (rat). Sodium borohydride is also flammable, corrosive, and extremely reactive with oxidizing agents, acids, alkalis, and moisture (*Sodium Borohydride;* MSDS No. S9125; Sigma-Aldrich Co.: Saint Louis, MO Nov. 1, 2015.

Consumers are increasingly expressing a preference for natural materials over synthetic or semi-synthetic ones. Thus, a need exists not only to provide compositions employing natural materials as bittering agents for beer and other beverages, but also processes for more natural production of said materials.

Biocatalytic production is an emerging technology which provides highly selective, safe, clean, and scalable production of high value compounds. Biocatalytic production relies on naturally occurring enzymes to replace chemical catalysts.

Enzymes are naturally occurring proteins capable of catalyzing specific chemical reactions. Enzymes exist in nature that are currently capable of replacing chemical catalysts in the production of modified hop bittering compounds (Robinson, P. K., Enzymes: principles and biotechnological applications. Essays Biochem 2015, 59, 1-41.).

Humulone is a natural secondary metabolite that would be exposed to fungi and bacteria cohabitating with the plant, *Humulus lupulus*. It is possible that soil- and plant-dwelling fungi and bacteria possess enzymes capable of modifying humulone for detoxification or scavenging purposes. Additionally, organisms may have evolved enzymes to modify humulone-like molecules, but because of promiscuous activity, these enzymes possess activity against the compounds of interest, isoalpha acids (Hult, K.; Berglund, P., Enzyme promiscuity: mechanism and applications. Trends Biotechnol. 2007, 25 (5), 231-238; Nobeli, I.; Favia, A. D.; Thornton, J. M., Protein promiscuity and its implications for biotechnology. Nat. Biotechnol. 2009, 27 (2), 157-167.).

Enzymes which catalyze oxidation/reduction reactions, that is transfer of hydrogen and oxygen atoms or electrons from one substance to another, are broadly classified as oxidoreductases. More specifically, enzymes that reduce ketone groups to hydroxyl groups are known as ketoreductases or carbonyl reductases and depend on the supplementation of an exogenous source of reducing equivalents (e.g. the cofactors NADH, NADPH). Consistent with the existing naming of the enzymes characterized herein, the enzymes will be referred to as a "ketoreductases".

The cost of expensive cofactors (NADH, NADPH) can be reduced by including additional enzymes and substrates for cofactor recycling, for example glucose dehydrogenase and glucose, or by utilizing a ketoreductase that is also capable of oxidizing a low-cost and natural feedstock, such as ethanol.

Abundant precedence exists for the utility of enzymes in brewing and their favorable influence on the final character of beer (Pozen, M., Enzymes in Brewing. Ind. Eng. Chem, 1934, 26 (11), 1127-1133.). The presence of yeast enzymes in the natural fermentation of beer is known to produce compounds that affect the flavor and aroma of the final beverage (Praet, T.; Opstaele, F.; Jaskula-Goiris, B.; Aerts, G.; De Cooman, L., Biotransformations of hop-derived aroma compounds by *Saccharomyces cerevisiae* upon fermentation. Cerevisia, 2012, 36, 125-132.). Exogenously added enzymes provide a variety of improvements to the brewing process, such as reduced viscosity, increased fermentable sugars, chill-proofing and clarification (Wallerstein, L. (1947) Bentonite and Proteolytic Enzyme Treatment of Beer, U.S. Pat. No. 2,433,411.; Ghionno, L.; Marconi, O; Sileoni, V.; De Francesco, G.; Perretti, G., Brewing with prolyl endopeptidase from *Aspergillus niger*: the impact of enzymatic treatment on gluten levels, quality attributes, and sensory profile. Int. J. Food Sci. Technol, 2017, 52 (6), 1367-1374.). Additionally, hop extracts have been specifically pretreated with enzymes for modifying hop-derived aroma compounds (Gros, J.; Tran, T. T. H.; Collin, S., Enzymatic release of odourant polyfunctional thiols from cysteine conjugates in hop. J. Inst. Brew. 2013, 119 (4), 221-227.).

Prior to the present invention, however, enzymes capable of catalyzing the reduction of isoalpha acids to dihydro-(rho)-isoalpha acids have not been observed in nature, and thus have not been described in the literature. The process disclosed herein represents a novel enzymatic reaction.

OBJECT OF THE INVENTION

It is an object of the present invention to provide a process for enzymatic production of dihydro-(rho)-isoalpha acids, a modified version of natural bittering agents derived from the hop plant. The present process is designed to replace current production processes which utilize the chemical reagent, sodium borohydride. It is a further object of the invention to provide novel enzyme catalysts which may be employed in such a process.

SUMMARY OF THE INVENTION

The present invention relates to a process that can be scaled up to industrial levels for bioconversion of iso-alpha acids into dihydro-(rho)-isoalpha acids, which can then be used as a naturally derived and light stable bittering agent in beverages.

One aspect of the present invention is a process for the high-yield bioconversion of iso-alpha acids into dihydro-(rho)-isoalpha acids utilizing a ketoreductase enzyme or a microorganism expressing a gene that encodes said ketoreductase.

A further aspect of the invention relates to such a process for production of dihydro-(rho)-isoalpha acids, wherein the process is carried out in an aqueous system with mild temperature and pH conditions, making it an environmentally benign manufacturing process.

In an embodiment of the invention, bioconversion of isoalpha acids to dihydro-(rho)-isoalpha acids comprises the addition of purified ketoreductase enzyme and NADPH or NADP to a mixture of isoalpha acids followed by incubation until the desired yield is obtained.

In another embodiment of the invention, bioconversion of isoalpha acids to dihydro-(rho)-isoalpha acids comprises the addition of purified ketoreductase enzyme and NADPH or NADP to a mixture of isoalpha acids in the presence of isopropanol for cofactor recycling, followed by incubation until the desired yield is obtained.

In a further embodiment of the invention, the concentration of isoalpha acids, i.e. the substrate, is maximized to increase the volumetric productivity of the bioconversion.

In a further embodiment of the invention, the concentration of the cofactor NADPH or NADP in the mixture is minimized to improve the economics of the bioconversion.

In an embodiment of the invention, bioconversion of isoalpha acids to dihydro-(rho)-isoalpha acids comprises the addition of purified ketoreductase enzyme and NADPH or NADP to a mixture of isoalpha acids in the presence of another enzyme (such as glucose dehydrogenase) for cofactor recycling, followed by incubation until the desired yield is obtained.

In another embodiment of the invention, bioconversion of isoalpha acids to dihydro-(rho)-isoalpha acids comprises the addition of a whole cell biocatalyst to a mixture of isoalpha acids followed by incubation until the desired yield is obtained, wherein the whole cell biocatalyst is an immobilized microorganism expressing the gene which encodes a ketoreductase.

In another embodiment of the invention, bioconversion of isoalpha acids to dihydro-(rho)-isoalpha acids comprises the feeding of isoalpha acids to a growing microorganism expressing the gene which encodes a ketoreductase.

In another embodiment of the invention, bioconversion of isoalpha acids to dihydro-(rho)-isoalpha acids comprises the addition of thermostable ketoreductase enzyme to an extract of alpha acids wherein heat is applied, and the mixture is incubated until the desired yield of dihydro-(rho)-isoalpha acids is achieved.

The present invention also relates to novel enzyme catalysts which may be utilized in the process of the invention as defined above.

A reductase according to the present invention optionally displays activity for reducing the carbonyl group in the side chain at C(4) of the isoalpha acids, converting the light-sensitive acyloin group to a secondary alcohol, and producing a light-stable isoalpha acid derivative (FIG. 1).

In another embodiment of the invention, the ketoreductase employed in the process according to the present invention advantageously displays minimal or no preference for catalyzing reduction of any one particular member of the six major isoalpha acids: cis-isohumulone, trans-isohumulone, cis-isocohumulone, trans-isocohumulone, cis-isoadhumulone, and trans-isoadhumulone.

In another embodiment of the invention, the ketoreductase employed in the process according to the present invention specifically reduces cis-isohumulone, cis-isocohumulone, and cis-isoadhumulone.

In another embodiment of the invention, the ketoreductase employed in the process according to the present invention specifically reduces trans-isohumulone, trans-isocohumulone, and trans-isoadhumulone.

In another embodiment of the invention, a mixture of 2 or more ketoreductase enzymes displaying the above substrate specificity is employed in the process according to the present invention to reduce a mixture of cis- and trans-isoalpha acids, to their respective dihydroisoalpha acids.

In another embodiment of the invention, a mixture of 2 or more ketoreductase enzymes displaying substrate specificity can be added to a reaction mixture to produce a unique mixture of dihydroisoalpha acids that is distinct from that produced by chemical reducing agents, such as sodium borohydride.

In a further embodiment, the present invention relates to a process as defined above, wherein the reductase enzyme is a ketoreductase.

A further embodiment of the invention relates to a process as defined above, wherein the ketoreductase enzyme or microorganism expressing a gene which encodes the ketoreductase enzyme comprises the amino acid sequence of SEQ ID NO:2, SEQ ID NO:3, SEQ ID NO:6, SEQ ID NO:8, SEQ ID NO:12, SEQ ID NO:13, SEQ ID NO:16, SEQ ID NO:19, SEQ ID NO:20, or SEQ ID NO:22.

In a further embodiment, the present invention relates to a process as defined above, wherein the ketoreductase enzyme or microorganism expressing a gene which encodes the ketoreductase can optionally have one or more differences at amino acid residues as compared to the ketoreductase enzyme selected from SEQ ID NO:2, SEQ ID NO:3, SEQ ID NO:6, SEQ ID NO:8, SEQ ID NO:12, SEQ ID NO:13, SEQ ID NO:16, SEQ ID NO:19, SEQ ID NO:20, and SEQ ID NO:22.

A further embodiment of the invention relates to a ketoreductase enzyme or microorganism expressing a gene which encodes the ketoreductase enzyme which comprises the amino acid sequence of SEQ ID NO:2, SEQ ID NO:3, SEQ ID NO:6, SEQ ID NO:8, SEQ ID NO:12, SEQ ID NO:13, SEQ ID NO:16, SEQ ID NO:19, SEQ ID NO:20, or SEQ ID NO:22.

A further embodiment of the present invention relates to a ketoreductase enzyme or microorganism expressing a gene which encodes the reductase can optionally have one or more differences at amino acid residues as compared to the reductase enzyme sequence of SEQ ID NO:2, SEQ ID NO:3, SEQ ID NO:6, SEQ ID NO:8, SEQ ID NO:12, SEQ ID NO:13, SEQ ID NO:16, SEQ ID NO:19, SEQ ID NO:20, or SEQ ID NO:22.

A further embodiment of the invention relates to a ketoreductase enzyme or microorganism expressing a gene which encodes the ketoreductase enzyme which is 99, 95, 90, 85, 80, 75 or 70 percent homologous to the ketoreductase enzyme selected from SEQ ID NO:2, SEQ ID NO:3, SEQ ID NO:6, SEQ ID NO:8, SEQ ID NO:12, SEQ ID NO:13, SEQ ID NO:16, SEQ ID NO:19, SEQ ID NO:20 and SEQ ID NO:22.

Another aspect of the invention comprises a vector comprising a polynucleotide encoding the amino acid sequence of SEQ ID NO:2, SEQ ID NO:3, SEQ ID NO:6, SEQ ID NO:8, SEQ ID NO:12, SEQ ID NO:13, SEQ ID NO:16, SEQ ID NO:19, SEQ ID NO:20, or SEQ ID NO:22.

The invention further comprises such a vector, further comprising at least one control sequence.

The invention further comprises a host cell comprising such a vector comprising a polynucleotide encoding the amino acid sequence of SEQ ID NO:2, SEQ ID NO:3, SEQ ID NO:6, SEQ ID NO:8, SEQ ID NO:12, SEQ ID NO:13, SEQ ID NO:16, SEQ ID NO:19, SEQ ID NO:20, or SEQ ID NO:22.

The invention further comprises a method for producing a ketoreductase of SEQ ID NO:2, SEQ ID NO:3, SEQ ID NO:6, SEQ ID NO:8, SEQ ID NO:12, SEQ ID NO:13, SEQ ID NO:16, SEQ ID NO:19, SEQ ID NO:20, or SEQ ID NO:22, comprising culturing said host cell under conditions that the ketoreductase is produced by said host cell.

The invention further comprises a method for producing a ketoreductase of SEQ ID NO:2, SEQ ID NO:3, SEQ ID NO:6, SEQ ID NO:8, SEQ ID NO:12, SEQ ID NO:13, SEQ ID NO:16, SEQ ID NO:19, SEQ ID NO:20, or SEQ ID NO:22, further comprising the step of recovering the ketoreductase produced by said host cell.

BRIEF DESCRIPTION OF THE DRAWINGS

FIG. 4 shows a structural model of reductase R17 (dark gray, surface rendering) with a representative substrate (trans-isohumulone, black) and cofactor (NADPH, light gray) bound to the active site cavity.

FIG. 6 shows an amino acid sequence alignment, generated with Clustal Omega (www.ebi.ac.uk/Tools/msa/clustalo/) of active ketoreductase homologs: R4, R17, R20, R21, and R23. A shared domain, containing 3 regions of good (solid line) or low homology (dashed line), are highlighted in boxes. An * (asterisk) indicates positions which have a single, fully conserved residue. A : (colon) indicates conservation between groups of strongly similar properties—scoring>0.5 in the Gonnet PAM 250 matrix.A . (period) indicates conservation between groups of weakly similar properties—scoring=<0.5 in the Gonnet PAM 250 matrix. Therefore the hierchy of conservation using these symbols is * (identical)>: (colon)>. (period).

DETAILED DESCRIPTION OF THE INVENTION

Figure 1:
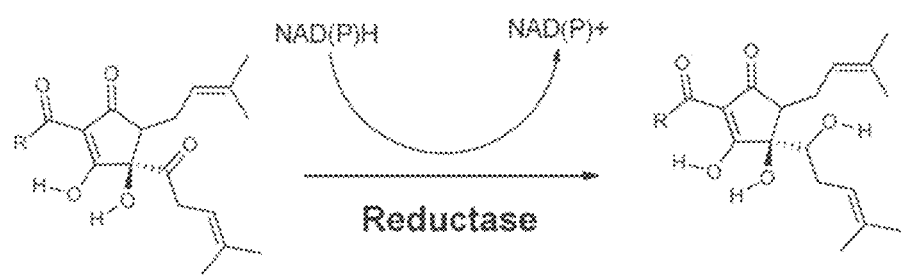
FIG. 1 shows the enzyme catalyzed reduction of a representative epimer of isoalpha acids.

In this invention, a ketoreductase enzyme replaces the function of sodium borohydride and allows a more natural production method for the beverage additive, dihydro-(rho)-isoalpha acids. The enzyme may be any ketoreductase specifically reducing a ketone group to a hydroxy group of any or all isomers of isoalpha acid (co-, n- ad-, and cis/trans-). The enzyme may be derived from, but not limited to, bacteria, fungi, or plants. The enzyme may be cofactor dependent (NADH or NADPH) or independent.

Herein, "isoalpha acids", "hop isoalpha acids", and "hop-derived isoalpha acids" may be used interchangeably.

According to the instant invention, an isoalpha acid solution is subjected to enzymatic treatment using one or more purified enzyme or a mixture containing the enzyme(s) and optionally additional enzymes for cofactor recycling. The amount of enzyme depends on the incubation parameters including duration, temperature, amount and concentration of substrate.

Alternatively, an isoalpha acid solution is subjected to enzymatic treatment using a mixture containing a microorganism expressing said enzyme(s). The invention furthermore provides a process for reducing isoalpha acids according to the invention, which comprises cultivating a ketoreductase-producing microorganism, if appropriate inducing the expression of the ketoreductase. Intact cells can be harvested and added directly to a reaction, in place of isolated enzyme, for the reduction of isoalpha acids as described above. Furthermore, the harvested cells can be immobilized prior to addition to a reduction reaction. The microorganism can be cultivated and fermented by known methods. The microorganism can be bacteria or fungi.

A mixture of cis- and trans-isoalpha acids may be incubated with a single ketoreductase displaying the capacity to reduce both isomers. Alternatively, a mixture of cis- and trans-isoalpha acids may be incubated with 2 or more ketoreductases showing varying specificity where the resulting product is a mixture of cis- and trans-dihydroisoalpha acids.

Alternatively, a solution containing only cis-isoalpha acids may be incubated with ketoreductase(s) specific for the cis- isomer, and the resulting product is a solution of cis-dihydroisoalpha acids. A solution of only cis-dihydroisoalpha acids may display advantageous bitterness and/or thermal stability properties.

Alternatively, a solution containing only trans-isoalpha acids may be incubated with ketoreductase(s) specific for the trans- isomer, and the resulting product is a solution of trans-dihydroisoalpha acids. A solution of only trans-dihydroisoalpha acids may display advantageous bitterness properties.

Customized blends of trans- and cis-isoalphacids may be incubated with 1 or more ketoreductases displaying variable substrate specificity, to produce unique blends of dihydroisoalpha acids otherwise unattainable.

An isoalpha acid mixture may be subjected to an enzymatic reaction using ketoreductase enzyme(s) in addition to enzymes for catalyzing additional desired modifications, such as but not limited to, dehydrogenases, isomerases, hydratases and lyases. Enzymes of varying activity may be combined in a one pot reaction or added sequentially.

A suitable solvent to use in enzyme incubation includes water and mixtures of water with another solvent compatible with the enzyme, such as ethanol or isopropanol. Enzymatic activity benefits from buffering of aqueous solutions. Buffering agents include, but are not limited to: tris(hydroxymethyl)aminomethane (aka. Tris), 4-(2-hydroxyethyl)piperazine-1-ethanesulfonic acid (aka. HEPES), sodium phosphate, and potassium phosphate.

The enzyme(s) and isoalpha acids are incubated within a suitable pH range, for example pH 6 to 10, and temperature range, for example 10 to 90° C., and held at this temperature for a sufficient time to convert isoalpha acids to the desired dihydro-(rho)-isoalpha acids yield. Continuous stirring will ensure a constant temperature and exposure of substrate to enzyme. The reaction duration, typically 24 to 48 hours, will depend on the amount and concentration of the enzyme and substrate, solvent present, and temperature chosen.

The enzyme(s) may be free in solution, immobilized onto beads or similar mixable scaffolds, or immobilized onto a film or resin over which a solution of isoalpha acids is passed. The purity level of the enzyme may vary from 30 to 90+% depending on the purification method.

The enzyme(s) may be removed from the final product via physical filtering or centrifugation. The enzyme(s) may also be rendered inactive by extreme temperature or pH and remain in the final product.

Reductase enzymes encompassed by the present invention include ketoreductase enzymes.

Details for 23 successfully purified enzymes are listed in Table 1, including: shorthand label, sequence ID number, and amino acid sequence.

TABLE 1

Purified reductases.

| Label | SEQ ID NO. | Amino Acid Sequence |
|---|---|---|
| R1 | 1 | MSSGIHVALVTGGNKGIGLAIVRDLCRLFSGDVVLTARDVTRGQAAVQQLQAEGLSPRFH<br>QLDIDDLQSIRALRDFLRKEYGGLDVLVNNAGIAFKVADPTPPHIQAEVTMKTNFFGTRD<br>VCTELLPLIKPQGRVVNVSSIMSVRALKSCSPELQQKFRSETITEEELVGLMNKFVEDTK<br>KGVHQKEGWPSSAYGVTKIGVTVLSRIHARKLSEQRKGDKILLNACCPGWVRTDMAGPKA<br>TKSPEEGAETPVYLALLPPDAEGPHGQFVSEKRVEQW |
| R2/3 | 2 | MRLEGKVCLITGAASGIGKATTLLFAQEGATVIAGDISKENLDSLVKEAEGLPGKVDPYV<br>LNVTDRDQIKEVVEKVVQKYGRIDVLVNNAGITRDALLVRMKEEDWDAVINVNLKGVFNV<br>TQMVVPYMIKQRNGSIVNVSSVVGIYGNPGQINYAASKAGVIGMTKTWAKELAGRNIRVN<br>AVAPGFIETPMTEKLPEKARETALSRIPLGRFGKPEEVAQVILFLASDESSYVTGQVIGI<br>DGGLVI |
| R4 | 3 | MSVFVSGANGFIAQHIVDLLLKEDYKVIGSARSQEKAENLTEAFGNNPKFSMEVVPDISK<br>LDAFDHVFQKHGKDIKIVLHTASPFCFDITDSERDLLIPAVNGVKGILHSIKKYAADSVE<br>RVVLTSSYAAVFDMAKENDKSLTFNEESWNPATWESCQSDPVNAYCGSKKFAEKAAWEFL<br>EENRDSVKFELTAVNPVYVFGPQMFDKDVKKHLNTSCELVNSLMHLSPEDKIPELFGGYI<br>DVRDVAKAHLVAFQKRETIGQRLIVSEARFTMQDVLDILNEDFPVLKGNIPVGKPGSGAT<br>HNTLGATLDNKKSKKLLGFKFRNLKETIDDTASQILKFEGRI |
| R5 | 4 | MNQVVLVTGGSSGIGKSICLYLHEKGYIVYGTSRNPARYAHEVPFKLIALDVLDDTTITP<br>ALKTIIDAEGKLDVLVNNAGIGMLGSIEDSTAEEVKEVFETNVYGILRTCQAVLPHMRER<br>KMGLIINVSSIAGYMGLPYRGIYSATKASVHMITEAMRMELKPYGVHACVVDPGDFATNI<br>SDNRKVAHAGRSGSVYMEEINRIEAMINAEVAHSSDPLLMGKAIEKIIRSSNPDINYLVG<br>KPMQKLSILVRRLVPKKWFEKIIASHYNMPVK |
| R6 | 5 | MANSGEGKVVCVTGASGYIASWLVKFLLSRGYTVKASVRDPSDPKKTQHLVSLEGAKERL<br>HLFKADLLEQGSFDSAIDGCHGVFHTASPFFNDAKDPQAELIDPAVKGTLNVLNSCAKAS<br>SVKRVVVTSSMAAVGYNGKPRTPDVTVDETWFSDPELCEASKMWYVLSKTLAEDAAWKLA<br>KEKGLDIVTINPAMVIGPLLQPILNTSAAAILNLINGAKTFPNLSFGWVNVKDVANAHIQ<br>AFEVPSANGRYCLVERVVHHSEIVNILRELYPNLPLPERCVDENPYVPTYQVSKDKTRSL<br>GIDYIPLKVSIKETVESLKEKGFAQF |
| R7 | 6 | MTLSSAPILITGASQRVGLHCALRLLEHGHRVIISYRTEHASVTELRQAGAVALYGDFSC<br>ETGIMAFIDLLKTQTSSLRAVVHNASEWLAETPGEEADNFTRMFSVHMLAPYLINLHCEP<br>LLTASEVADIVHISDDVTRKGSSKHIAYCATKAGLESLTLSFAARFAPLVKVNGIAPALL<br>MFQPKDDAAYRANALAKSALGIEPGAEVIYQSLRYLLDSTYVTGTTLTVNGGRHVK |
| R8 | 7 | MSLQGKVALVTGASRGIGQAIALELGRQGATVIGTATSASGAERIAATLKEHGITGTGME<br>LNVTSAESVEAVLAAIGEQFGAPAILVNNAGITRDNLMLRMKDDEWFDVIDTNLNSLYRL |

TABLE 1-continued

Purified reductases.

| Label | SEQ ID NO. | Amino Acid Sequence |
|---|---|---|
| | | SKGVLRGMTKARWGRIISIGSVVGAMGNAGQANYAAAKAGLEGFSRALAREVGSRGITVN SVTPGFIDTDMTRELPEAQREALQTQIPLGRLGQADEIAKVVSFLASDGAAYVTGATVPV NGGMYM |
| R9 | 8 | MDLTNKVVVVTGGSAGLGEQICYEAAKQGAVVVVCARRINLIGKVREQCAVLSGREAFSY QLDIADPESVERVVEAISAEVGPIDVLVNNAGFGLFENFVEIDLAVARQMFDVNVLGMMT FTQKVAIKMIEAGQGHIINVASMAGKMATAKSTVYSATKFAVLGFSNALRLELKPLGVAV TTVNPGPIQTEFFDKADPTGTYLAAVDKIVLDPTKLAKEVVGSMGTSRREINRPFVMEAA ARFYTLFPHLGDFIAGNILNKK |
| R10 | 9 | MRRILITGANGFVGQILCSMLRQAGHHVIALVGAESALSSHADESVRCDIRDASGLEQAL CRAAPTHVVHLAAITHVPTSFNNPVLTWQTNVMGSVNLLQALQRSAPEAFVLFVSSSEVY GETFKQGTALGEDSACKPMNPYAASKLAAEAAFNEYFRQGRKGIVVRPFNHIGARQSPDF ATASFARQIALIEAGKQAPQLKVGNLQAARDFLDVHDVCDAYVALLQLADEQERYPGCLN ICRGEPTSLQTLLTQLMALSSSVIEVTIDPDRMRPSDIPSAFGNNSAMRCATGWKPKTKL DDTLEALLNYVVRHEVISAV |
| R11 | 10 | MSLLLEPYTLRQLTLRNRIAVSPMCQYSSVDGLANDWHLVHLGSRAVGGAGLVISEAMAV TPDGRITPEDLGLWNDEQIEPLQRITRFINTQGAVAGIQLAHAGRKASTWRPWLGKHGSV PLTEGGWTPVGPSAIAFDPQHTAPLQLSETQIQELIKAFVDSARRALTAGFKVVEIHAAH GYLLHQFLSPLSNQRTDQYGGSFENRIRLTLQVTEAVRAVWPQELPLFVRVSATDWVEDG WNAEETVELARRLKALGTDLIDVSSGGTSANAEIPVGPGYQTRFAEQVRKEADIATGTVG MITDPAQAEHILRTGQADIILLARELLRDPYWPLRADEDLGGRQATVVPAQYQRATHRDQ PIHESDLRD |
| R12 | 11 | MSSSSLRVLAIGNNPNILFYTSRFQLAKNIDLYHVNDSKSCQFEIETEYYGKDRFELENH FTSIEHLTEALSSKSSEAVFDIIIMSAPSLQELSSLASKLTSIIDSNTKIFLESSGFIQL EPFVKLSMESPHVNVFSILTDLDIRQIGPNHFKHFPSTAKENTIYLGESKSSTEKYSSGV ITLLTTFEKLFAKLFSNIKINLCNFSSIEFLSQQWKLAISRICFDPLLIMFEQENPSDLD QQIIAKPLISGLVTEIITVAKTMGARLNSSHDNENSLLSLWKNSYHSTNKPPALVYHFIH QTTPLNIDILLLQTILLADDFGIKTPYLEFLYSVLSQFERLNSG |
| R13 | 12 | MEYRKVGKWGVKISELSLGSWLTFGKQLDLDTATEVVKKAFNSGINFFDTAEAYAGGIAE AMLGKILKNFRREDLVVSTKIFWGGSGPNDLGLSKKHLLEGTWNSLKRLQMDYVDILYCH RPDPNVPMEEVVFAMDYILREGLALYWGTSEWSAKEIEEAHRVCKELGVMPPIVEQPQYN MFVRERVEKEYAPLYEKYGMGLITYSPLASGLLSGKYNNGIPEGSRLATFPQVRKWLEEG GLLNEKTFKKLRKLQNIADQLGASLPQLAIAWILKNKNVSSVILGVSRPEQLEENLKAVE IKEKLTEDVMEEIEKILNE |
| R14 | 13 | MTLANLPPLVTVFGGSGFVGRHVVRMLAKRGYRIRVAVRRPDLAGFLQPLGNVGQISFAQ ANLRYRDSIIKAVEDADHVVNCVGILAESGRNTFDAVQEFGAKAIAEAARDTGATLTHIS AIGADANSQTGYGRTKGRAEAAIHSVLPGAVILRPSIIFGPEDDFFNKFAKMARNLPFLP LIGGGKTKFQPVYVEDVAEAVARSVDGKLKPGAIYELGGPDVMTFRDCLEAVLAATYRER SFVNLPFGVASMIGKLASLVPLITPPLTPDQVTMLKKDNVVSAEAEKKGLTLEGIGITPV RVASVLPSYMVQYRQHGQFSNAGKAA |
| R15 | 14 | MTAEVFDPRALRDAFGAFATGVTVVTASDAAGKPIGFTANSFTSVSLDPPLLLVCLAKSS RNYESMTSAGRFAINVLSETQKDVSNTFARPVEDRFAAVDWRLGRDGCPIFSDVAAWFEC SMQDIIEAGDHVIIIGRVTAFENSGLNGLGYARGGYFTPRLAGKAVSAAVEGEIRLGAVL EQQGAVFLAGNETLSLPNCTVEGGDPARTLAAYLEQLTGLNVTIGFLYSVYEDKSDGRQN IVYHALASDGAPRQGRFLRPAELAAAKFSSSATADIINRFVLESSIGNFGIYFGDETGGT VHPIANKDAHS |
| R16 | 15 | MDEVILVTGAAKGIGLATVKRLSSQGARVILNVHHEIEATDWQALTAEYPRLTQLVGDVS DDQSAANLIDTVMTNFGRLDGLVNNAGVTHDQLLTRLHAEDFMSVIQTNLLGTFNMTKYA LKVMQRQRQGAIVNVASVVGLHGNVGQANYAASKAGIIGLTKTTAKEAARRQVRCNAVAP GMITTAMTAQLNDRVTAAALSDIPLKRFGTPDEIAQAIDFLLHQPYLTGQVLTVDGGMTI |
| R17 | 16 | MRVLLTGGSGFIAAHILDILLSRGHTVITTVRSQQKIDAIKAAHPDVPASKLDFFIVEDI AKENAFDECLKKFGEGLEAVLHTASPFHFNVTDTKKDLLDPAIIGTTAILHAIKKFAPSV TRVVVTSSFASIIDASKGNWPDHTYTEEDWNPITLSEAVENPSNGYRASKTFAEKAAWEF VEKENPNFTLSTMNPPLVLGPIVHYLNSLDALNTSNQRVRDVLQGKVVKEEIPIGTFIW IDVRDLALAHVKAIEIAEAAGKRFFITEGYFSNKEICEIIRKNFPEDGGELPGKEVKGGG YPEGGIYKFDNARTRSVLGLEFRGLEESIVDLVKSLKEVGV |
| R18 | 17 | MSRNLALVTGSTQGIGLAVAKELAIKHNYQVLLGVRNTKAGEEIASDLRKEGHEASVVEL DLTSADSIDKAVKHIDEKYGYLDVLINNAGVLLDRQEGLSTWDLFSKTFTTNVFGTGCLT QSLLPLLRKAKNSPPRIVFVTSVMGSLTKATDETTTYYNIDYKAYDASKAAVNMLMFNFA RELDAVGGKVNSVCPGLVKTGLTNYHEWGTSPETGAERIVEMATIGEDGPTKTISDRNGE LPL |
| R19 | 18 | MDLQNKRVLVTGSTQGIGAATALAFAQKGCQVLLNGRRPELPEEIADQLEKIGADYQYFS ADVSDEGAIKQLFKEIGEIDILVNNAGITKDQIMIGMKLADFDQVIKVNLRSSFMLTQKA LKKMLKKRSGAIINMASIVGQHGNAGQANYAASKAGVIALTQTAAKEAAGRGVRVNAIAP GMIASQMTAVLPDEVKEQALSQIPLARFGKAEEVAQAAVFLAENDYVTGQTLVVDGGMTI |

TABLE 1-continued

Purified reductases.

| Label | SEQ ID NO. | Amino Acid Sequence |
|---|---|---|
| R20 | 19 | MTKVLVAGGSGFIGAHILEQLLAKGHSVVTTVRSKEKAQKILDAHKAEADRLEVAIVPEI AREDAFDEVVKTPGIEVVIHPASPCHLNFTDPQKELIDPAVLGTTNILRAIKRDAPQVRR VIITSSVAAIFNTKDPVSTLTEQSWNPNDLSNIHDSRAVAYCVSKTLAERAAWDYVDQEK PNFDLVTVNPPLVLGPVVGHFSNVDSINASNECLANLVRGKWRDEIPPTGPVNIWIDVRD VAAAHVRAMERQEAGGKRLFTVGGRFSYTKIAEIVREHGPDRFKDKMPRAEARSGDANYT GPVLKFDNGETNRILGIEVVTPLEKSVLDFVESIKEFDL |
| R21 | 20 | MTKVLLTGGSGFIAAHILEQLLAKNYTVITTVRTKSKADLIKEAHADLVKSGRLSVAIVP DIAVLSAFDDLVAKIASGPDGDLEYVVHTASPLFFTFTDAQKEIITPALNGTRGILEAVK RSAPKVKRVVITSSFAAILSEDDFTNPNATFSESSWNPDTVKDANRSIATGYHVSKVESE RLAWDFIKNEKPNFDLVTVNPPLVLGPVAHSLASVDAINASNERIADLLRGKWKAEIPET GAVDLYIDVRDTAKAHIKALELPEASGHRLFPVASRTSNHEIAKIIRDNFPEFAERLPGP EVKGGEHVDENKAYKWNCDETNKLLKIDWIPIEQSMIDTVNSLKDKGI |
| R22 | 21 | MPTVSPGSKVLVTGANGFIAIWVVRRLLEEGYSVRGTVRAASKASHLKDIFKSYGEKLEV VVVPDFTKEGAFDELIKGMDAIQHIASPGPANTDDLYEIVNPAVDGTLNLLNTALKHGSG LKRIVITSGAGAIIDTTTAWKFYNDHKNVIKWDLTVLNPVFVFGPPIHEIGASPMTLNSS MVHFINVNVISTDTPKTKEGLSFAASWVDVRDVAQGHVLALQKEAAGGERIILSEGSFVW QDWVDVANKFKSKRELPKGMPEIERVYKFQMDASKATRILGITYRSKEDTMKDLLEDFER RGW |
| R23 | 22 | MKVLLTGGSGFIATHCLDALLKHGHEVVITVRSAEKGQALVDLFKGQKVSYTIVKDISVP GAFDQAVISDPPFDAVVHTASPFHYDVQDNKRDLLDPAIIGTTGILESIQKGAPSVKKVV VTSSFAAISNPTAPPKVYDETVWNQMTMEEALTTKDPQAVYRGSKTFAEKAAWEFVEREK PNFTLTVLNPPVSHFLFSRHKDVAVTFFSDSFQHCRWSTARSCTPWHHWTISTPRASES |

Figure 2:
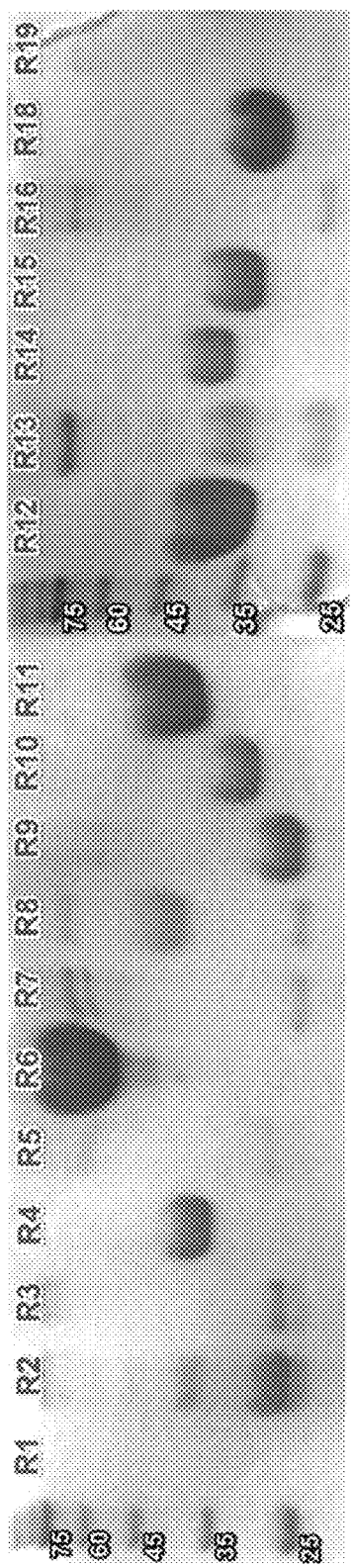
FIG. 2 shows an SDS-PAGE analysis of purified reductases.

Almost all candidates were sufficiently pure (>80% protein content is the protein of interest) after one-step purification (See FIG. 2).

Reductase enzymes encompassed by the present invention include those comprising the following amino acid sequences: SEQ ID NO:2, SEQ ID NO:3, SEQ ID NO:6, SEQ ID NO:8, SEQ ID NO:12, SEQ ID NO:13, SEQ ID NO:16, SEQ ID NO:19, SEQ ID NO:20, and SEQ ID NO:22.

Reductase enzymes encompassed by the present invention also include those having one or more differences at amino acid residues as compared to the following amino acid sequences: SEQ ID NO:2, SEQ ID NO:3, SEQ ID NO:6, SEQ ID NO:8, SEQ ID NO:12, SEQ ID NO:13, SEQ ID NO:13, SEQ ID NO:16, SEQ ID NO:19, SEQ ID NO:20, and SEQ ID NO:22.

Reductase enzymes encompassed by the present invention also include those comprising an amino acid sequence which is identical by at least 40% (including at least 50%, at least 60%, at least 70%, at least 80%, at least 85%, at least 90%, and at least 95%) to the following amino acid sequences: SEQ ID NO:2, SEQ ID NO:3, SEQ ID NO:6, SEQ ID NO:8, SEQ ID NO:12, SEQ ID NO:13, SEQ ID NO:13, SEQ ID NO:16, SEQ ID NO:19, SEQ ID NO:20, and SEQ ID NO:22.

As used herein, "percentage of sequence homology," "percent homology," and "percent identical" refer to comparisons between polynucleotide sequences or polypeptide sequences, and are determined by comparing two optimally aligned sequences over a comparison window, wherein the portion of the polynucleotide or polypeptide sequence in the comparison window may comprise additions or deletions (i.e., gaps) as compared to the reference sequence for optimal alignment of the two sequences. The percentage is calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Determination of optimal alignment and percent sequence homology is performed using the BLAST and BLAST 2.0 algorithms (See e.g., Altschul et al., J. Mol. Biol. 215: 403-410 [1990]; and Altschul et al., Nucleic Acids Res. 3389-3402 [1977]). Software for performing BLAST analyses is publicly available through the National Center for Biotechnology Information website.

Promiscuous enzymes may catalyze the same chemical reaction despite possessing low shared amino acid identity. Ketoreductase R4 (SEQ ID NO:3) was initially selected for screening due to its promiscuous nature [Guo et al. *Biochim. Biophys. Acta* 2014, 1844]. Five additional ketoreductases (R17 (SEQ ID NO:16), R20 (SEQ ID NO:19), R21 (SEQ ID NO:20), R22 (SEQ ID NO:21) and R23 (SEQ ID NO:22)) that contain the same enzyme domain (IPR001509: NAD-dependent epimerase/dehydratase) and share amino acid identity to R4 (SEQ ID NO:3) were acquired as synthetic genes, purified and characterized. Reductases were purposely selected at increasingly lower sequence identity in order to establish a sequence identity cutoff.

Despite sharing a relatively low percent identity (34-39% over entire length of the enzyme) to R4 (SEQ ID NO:3), enzymes R17 (SEQ ID NO:16), R20 (SEQ ID NO:19), R21 (SEQ ID NO:20) and R23 (SEQ ID NO:22) catalyze the transformation of isoalpha acids to dihydro-(rho)-isoalpha acids. R22 (SEQ ID NO:21) which shares 33% identity to R4 (SEQ ID NO:3) does not catalyze the transformation of isoalpha acids to dihydro-(rho)-isoalpha acids but is otherwise an active enzyme as purified (established by measuring enzyme-catalyzed oxidation activity of isopropanol).

A feature that separates functional from nonfunctional reductases for obtaining dihydro-(rho)-isoalpha acids is illustrated by a multiple sequence alignment (FIG. 6). Ketoreductase R4 (SEQ ID NO:3), and all R4 (SEQ ID NO:3) homologs characterized as capable of converting isoalpha acids to dihydro-(rho)-isoalpha acids herein, possess a domain occurring between residues 100 and 200, composed of 13 amino acids of good homology (>53% identity) and 9 amino acids of high homology (>55%) separated by 36-39 amino acids of low homology (38-46%). This domain is missing in the nonfunctional R22 polypeptide (SEQ ID NO:21). The domain is thus deemed a hallmark of ketoreductase activity for obtaining dihydro-(rho)-isoalpha acids.

Specific embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

As used herein, the term "comprising" or "comprises" is intended to mean that the compositions and methods include the recited elements, but not excluding others.

The term "effective amount" refers to that quantity of a reductase which is sufficient to transform isoalpha acids into dihydro-(rho)-isoalpha acids. Determination of an effective amount for a given administration is well within the ordinary skill in the pharmaceutical arts.

In a method for preparing dihydro-(rho)-isoalpha acids, an isoalpha acid solution is subjected to enzymatic treatment using one or more purified reductase enzymes or a mixture containing a reductase enzyme(s) and optionally additional enzymes for cofactor recycling, in an amount effective to transform the isoalpha acids into dihydro-(rho)-isoalpha acids, The amount of enzyme depends on the incubation parameters including duration, temperature, amount and concentration of substrate.

Alternatively, an isoalpha acid solution is subjected to enzymatic treatment using a mixture containing a microorganism expressing said enzyme.

A mixture of cis- and trans-isoalpha acids may be incubated with a single reductase/ketoreductase displaying the capacity to reduce both isomers. Alternatively, a mixture of cis- and trans-isoalpha acids may be incubated with 2 or more ketoreductases showing varying specificity where the resulting product is a mixture of cis- and trans-dihydroisoalpha acids.

Customized blends of trans- and cis-isoalphacids may be incubated with 1 or more reductases/ketoreductases displaying variable substrate specificity, to produce unique blends of dihydroisoalpha acids otherwise unattainable.

An isoalpha acid mixture may be subjected to an enzymatic reaction using a reductase enzyme in addition to enzymes for catalyzing additional desired modifications, such as but not limited to, dehydrogenases, isomerases, hydratases and lyases. Enzymes of varying activity may be combined in a one pot reaction or added sequentially.

A suitable solvent to use in the enzyme incubation includes water and mixtures of water with another solvent compatible with the enzyme, such as ethanol or isopropanol, Enzymatic activity benefits from buffering of aqueous solutions. Buffering agents include, but are not limited to: tris(hydroxymethyl)aminomethane (aka. Tris), 4-(2-hydroxyethyl)piperazine-1-ethanesulfonic acid (aka. HEPES), sodium phosphate, and potassium phosphate.

The enzyme and isoalpha acids are incubated within a suitable pH range, for example pH 6 to 10, and temperature range, for example 10 to 90° C., and held at this temperature for a sufficient time to convert isoalpha acids to the desired dihydro-(rho)-isoalpha acids yield. Continuous stirring will ensure a constant temperature and exposure of substrate to enzyme. The reaction duration, typically 24 to 48 hours, will depend on the amount and concentration of the enzyme and substrate, solvent present, and temperature chosen.

The reductase enzyme may be free in solution, immobilized onto beads or similar mixable scaffolds, or immobilized onto a film or resin over which a solution of isoalpha acids is passed. The purity level of the enzyme may vary from 30 to 90+% depending on the purification method.

The reductase may be removed from the final product via physical filtering or centrifugation. The enzyme may also be rendered inactive by extreme temperature or pH and remain in the final product.

The present invention is a novel method of utilizing reductases to transform isoalpha acids into dihydro-(rho)-isoalpha acids. Codon optimized reductase genes have achieved yields of upwards of 100 mg purified enzyme per L cell culture in *E. coli* BL21(DE3). All enzymes were characterized with NADPH as the cofactor. The reductases characterized in this study possess an enzymatic activity that has not been described previously. These enzymes form a basis for the novel biocatalysts which may be utilized in a novel biotransformation to replace current processes utilizing sodium borohydride.

EXAMPLES

The following examples illustrate the invention without limiting its scope.

Example 1—Reductase Preparation and Screening

Methods
Candidate Identification

Reductase candidates were selected after an extensive search of the literature for characterized enzymatic reactions of a similar nature to the desired reaction, followed by bioinformatic mining of three public protein sequence databases: UniProt (www.uniprot.org/), Pfam (//pfam.xfam.org/), and InterPro (www.ebi.ac.uk/interpro/*E. coli*). Bioinformatics relied on BLASTP sequence alignments (//blast.ncbi.nlm.nih.gov/Blast.cgi) between characterized enzymes and reductase candidates.

Enzyme Expression and Purification

Plasmid DNA was acquired in several manners: 1) in an expression vector from the DNASU Plasmid Repository (www.dnasu.org), 2) in a cloning vector from DNASU Plasmid Repository and subsequently cloned into an in-house expression vector, 3) as a synthetic gene in an expression vector from Atum (www.atum.bio), or 4) as a synthetic gene in an expression vector from General Biosystems (www.generalbiosystems.com). Synthetic genes were codon-optimized for expression in *E. coli*.

5 mL Luria Broth with appropriate antibiotics was inoculated from an agar plate of *E. coli* BL21 (DE3) containing the expression vector of interest and incubated at 30° C. with shaking overnight. The following day, the overnight culture was back-diluted 1:100 into fresh 0.5 L Luria Broth with antibiotics and incubated at 37° C. for 2-3 hr with 220 rpm shaking until an optical density of 0.5 was reached. Cultures were induced with 0.2 mM final concentration of isopropyl β-D-1-thiogalactopyranoside (IPTG) and incubated at 25° C. with 180 rpm shaking for 16 h. Cells were harvested by centrifugation at 4800 rpm for 15 min. The cell pellet was resuspended in 12 mL of Bind Buffer (10 mM HEPES, 50 mM NaCl, pH 7.5) and cells were lysed via sonication for 15 min (5 sec on, 5 sec off). Cell lysate was clarified via centrifugation at 10,000 rpm for 20 min. Tagged protein was purified from clarified cell lysate via cobalt affinity, maltose affinity, or glutathione affinity chromatography. Protein solutions were exchanged into Protein Storage Buffer (20 mM Tris-HCl, 50 mM NaCl pH 7.0) via centrifugal filtration. Protein concentration was measured via absorbance at 280 nm using extinction coefficients calculated by using the appropriate amino acid sequence. Glycerol added to a final concentration of 20% and enzyme solutions frozen at −20 or −80° C.

Isoalpha Acids Reduction Assay

Purified enzyme candidates were tested for their ability to reduce isoalpha acids. The specific reaction entails reducing a specific ketone group to a hydroxy group of any or all isomers and congeners of isoalpha acid (co-, n- ad-, and cis/trans-). In a 2 mL microcentrifuge tube, 100 uL of enzyme solution (final concentration of 0.15-1.8 mg/mL enzyme) was added to 900 uL of buffered aqueous solution with cofactor recycling by glucose dehydrogenase (263 mM sodium phosphate, 1.7 mM magnesium sulfate, 1.1 mM NADP+, 1.1 mM NAD+, 80 mM D-glucose, 4.3 U/mL glucose dehydrogenase, pH 7.0). 5 uL of alkaline isoalpha acid solution (ISOLONE®, 29% isoalpha acids) was added for a final concentration of 0.29% isoalpha acids. The reaction was incubated at 30° C. with orbital shaking at 180 rpm for 24 hours. The obtained reaction mixture was filtered to remove enzyme. Isoalpha acids and dihydro-(rho)-isoalpha acids were detected by UPLC-MS/MS. A negative control sample contains all the above reaction components where the enzyme solution was replaced with Protein Storage Buffer.

Results

Candidate Selection

Based on public functional annotations and amino acid sequence similarity, 60 unique enzyme sequences were identified as being reductase candidates.

Enzyme Expression and Purification 30 candidates were selected for expression and purification based on the availability of DNA and sufficient sampling of the diversity of amino acid sequences represented in the initial group of 60 candidates. Most candidates displayed good expression and solubility levels in the *E. coli* BL21 (DE3) with yields varying from 5 to 100 mg purified protein per liter culture. Several candidates were abandoned due to poor solubility in the host organism.

Reductase Characterization

Figure 3:
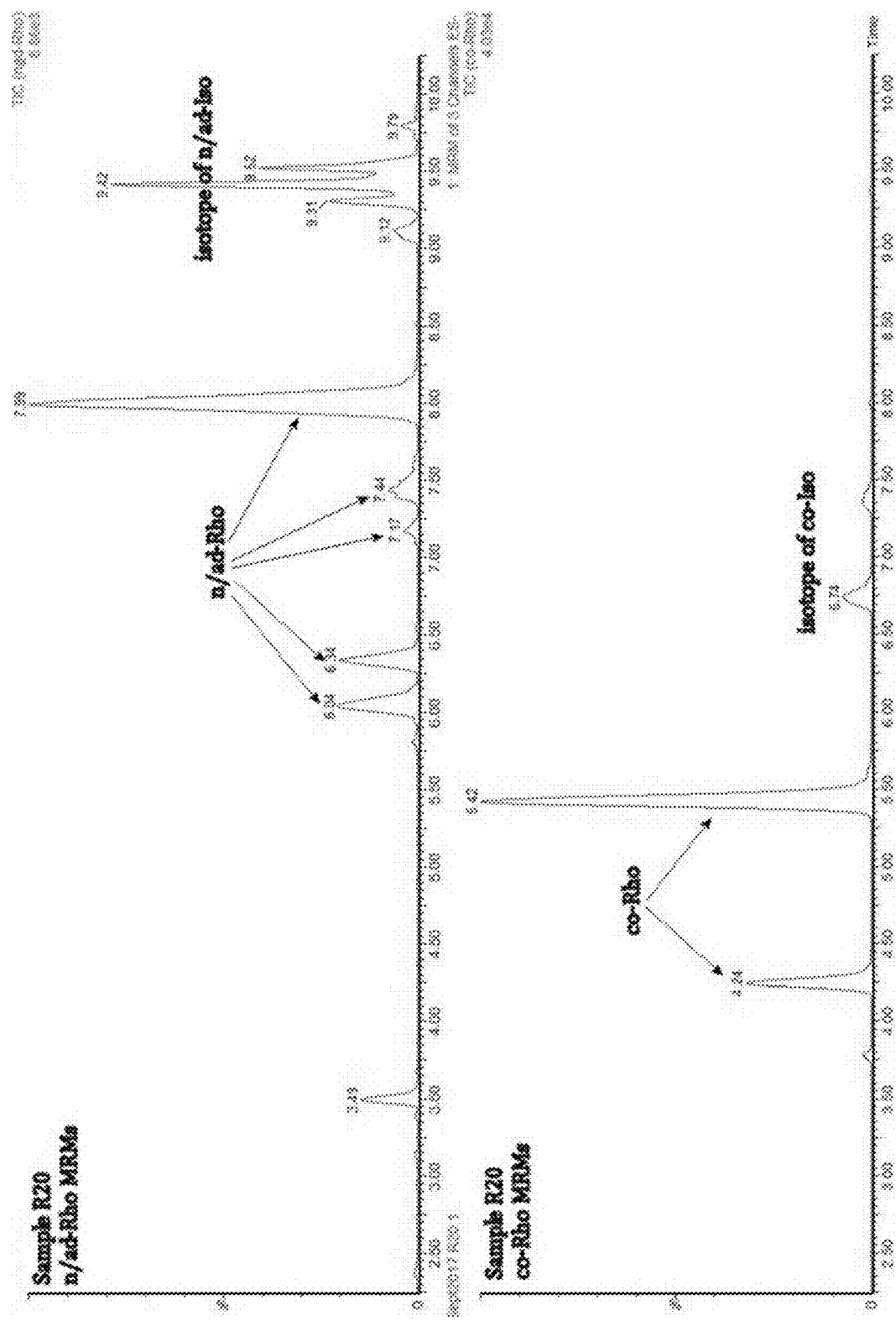
FIG. 3 shows UPLC chromatograms for isoalpha acids incubated with (top two panels) and without (bottom two panels) reductase R20 for 24 hr at 30° C. Peaks corresponding to the product, dihydro-(rho)-isoalpha acids, are indicated.
Figure 3:
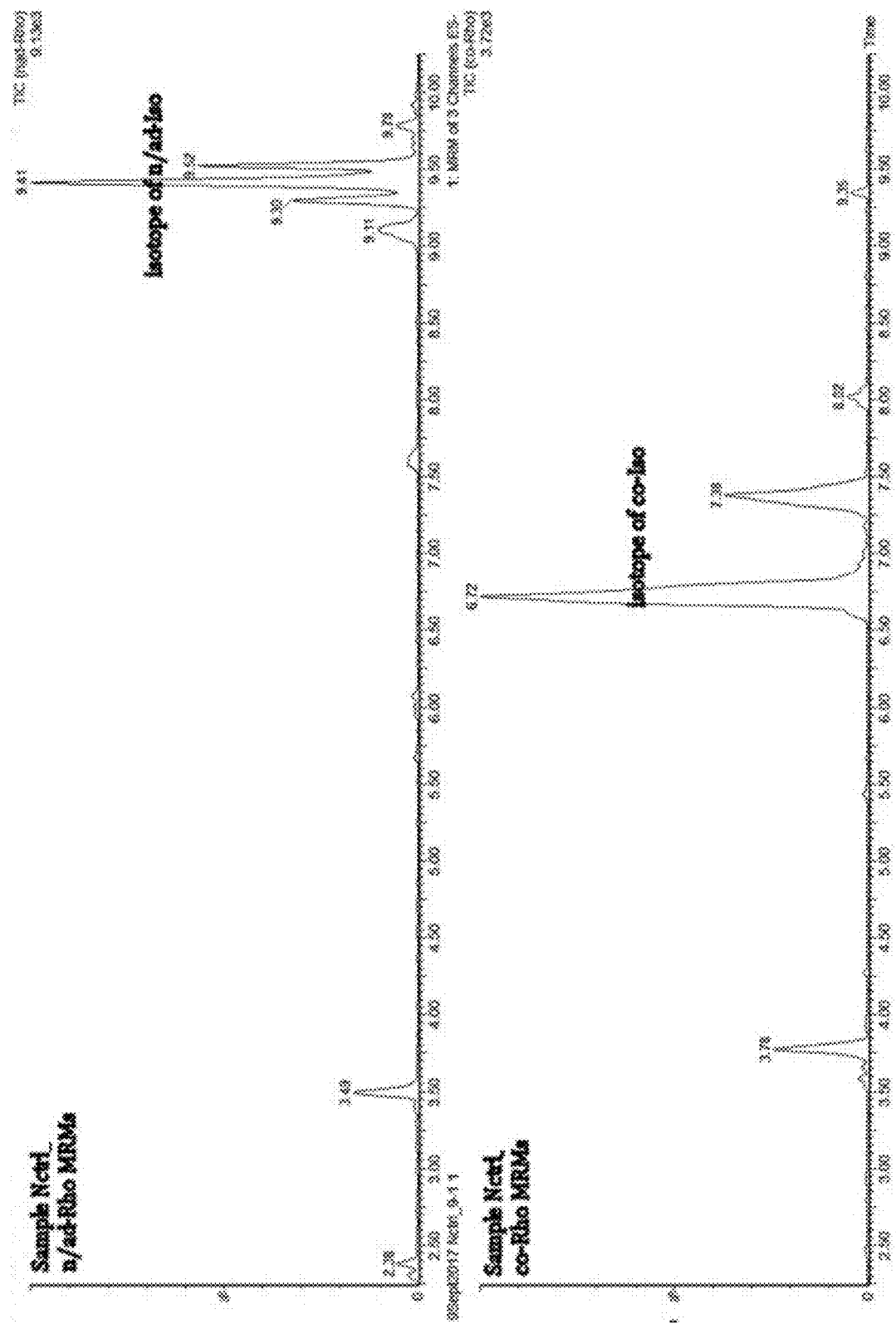

Enzymes were determined to reduce isoalpha acids if peaks corresponding to cis/trans- co/ad/n-dihydro-(rho)-isoalpha acid were detected via UPLC at a greater intensity than a control sample lacking enzyme. Ten unique enzymes were determined to be isoalpha acid reductases (See FIG. 3). Details of these enzymes are summarized in Table 2. Due to solubility and enzyme yield, the final concentration of in-house enzymes in the assay varied from 0.15-1.8 mg/mL. Lower enzyme concentration contributes to the dihydro-(rho)-isoalpha acids yield.

Enzymes were initially tested for reductase activity in the presence of glucose, glucose dehydrogenase, and NAD in order to recycle the NADP required for isoalpha acid reduction. After determination of reductase activity, enzymes were characterized for their ability to oxidize isopropanol, a more economical alternative for cofactor recycling. Ability to efficiently oxidize isopropanol is indicated in Table 2.

TABLE 2

Novel isoalpha acid reductases characterized.

| Label | Isoalpha Acid Reduction | Isopropanol Oxidation |
|---|---|---|
| R2 | Yes | No |
| R4 | Yes | Yes |
| R7 | Yes | No |
| R9 | Yes | Yes |
| R13 | Yes | No |
| R14 | Yes | Yes |
| R17 | Yes | Yes |
| R20 | Yes | Yes |
| R21 | Yes | Not Tested |
| R23 | Yes | Not Tested |

Substrate Specificity

The ideal ketoreductase for biotransformation purposes shows no substrate specificity for the isohumulone congeners which vary based on side chain composition (conferring n-, ad-, and co-isohumulone). Additionally, the ketoreductase shows no specificity for the isohumulone cis and trans isomers which vary spatially at the C4 tertiary alcohol group proximal to the site of enzymatic reduction. Substrate specificity is dictated by the amino acid sequence and thus the geometry of the substrate binding pocket of an enzyme. Larger binding pockets accommodate larger substrates, as well as a greater variety of substrates, compared to more restricted binding pockets. (See FIG. 4).

Figure 5A:
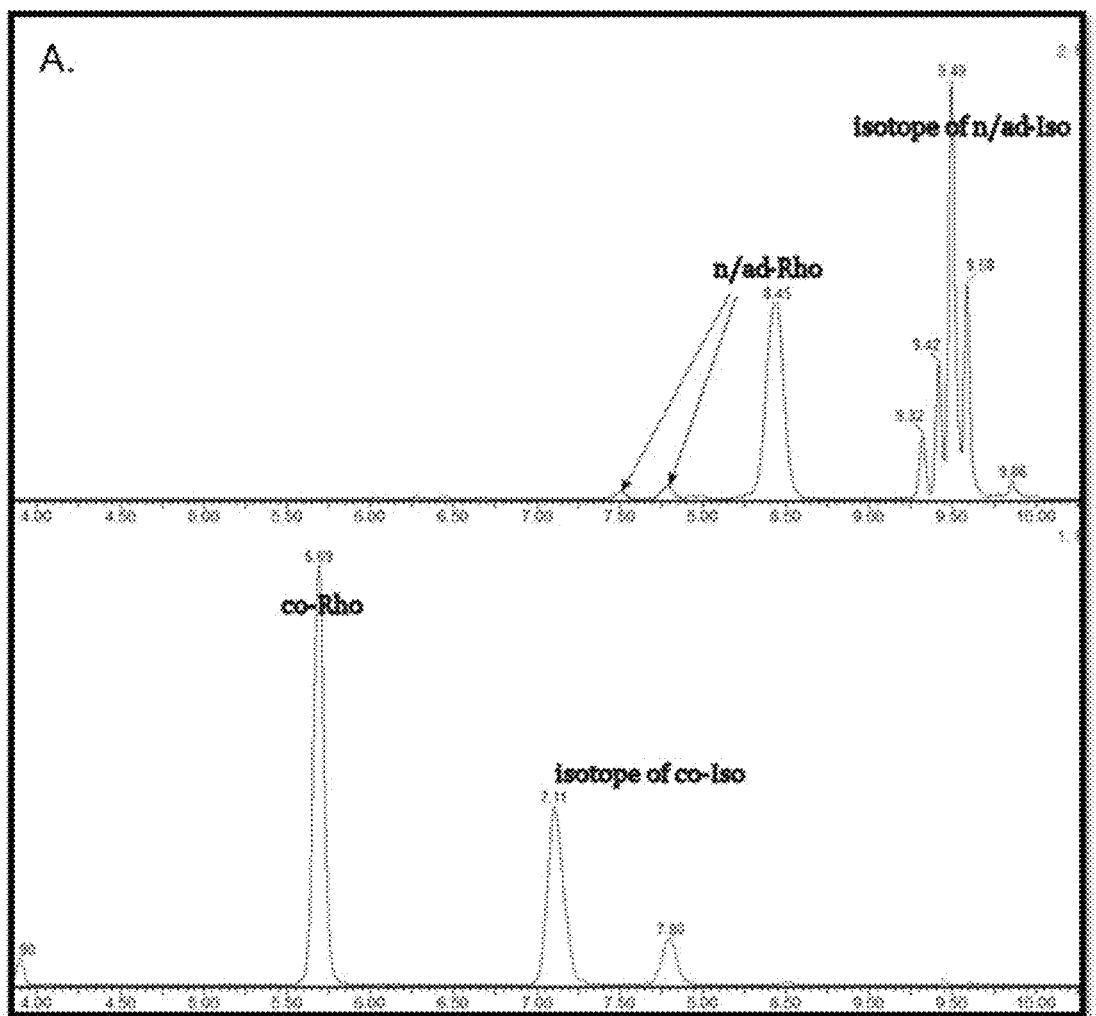
FIG. 5A shows UPLC chromatogram (A) for a ketoreductase that produces only one diastereomer of dihydro-(rho)-isoalpha acids and FIG. 5B shows UPLC chromatogram (B) for a ketoreductase that produces both diastereomers of dihydro-(rho)-isoalpha acids. Peaks corresponding to the product, dihydro-(rho)-isoalpha acids, are indicated.
Figure 5B:
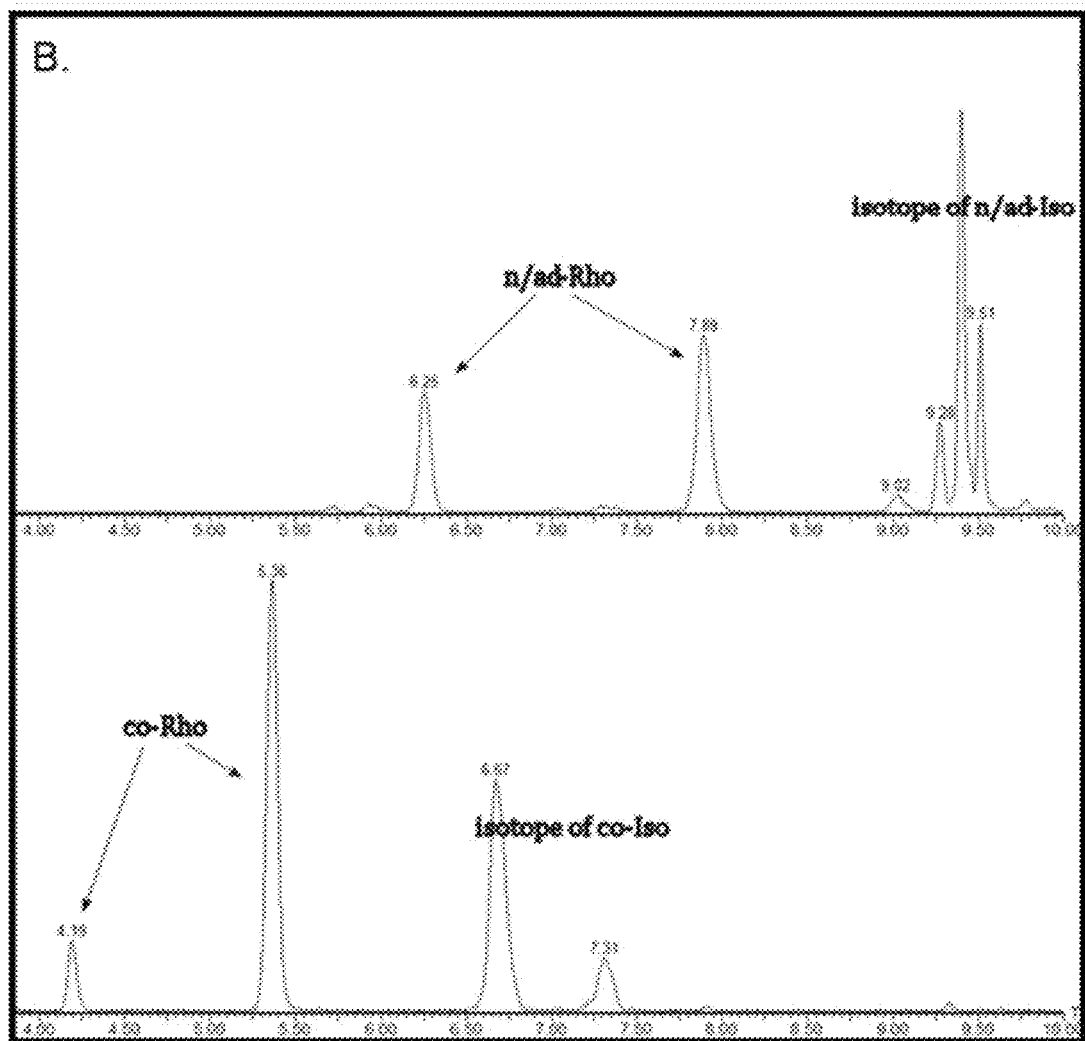

Two varieties of reduction stereospecificities were observed among the characterized reductases (See FIG. 5).

Despite the presence of two additional ketone groups on the isoalpha acid molecule, only the desired reduction at the C4 side chain was observed for all characterized ketoreductases.

Example 2—Enzyme Treatment of Hop Derived Isoalpha Acids with Cofactor Recycling by Isopropanol Oxidation In a 1.5 mL microcentrifuge tube, 10 mg reductase is resuspended in 700 uL of buffered aqueous solution (eg. Sodium Phosphate pH 7.5). 290 uL of isopropanol is added. 10 uL of alkaline isoalpha acid solution (29% isoalpha acids) is added for a final concentration of 0.29% isoalpha acids. The reaction is incubated at 30° C. with orbital shaking at 180 rpm for 48 hours. The obtained reaction mixture is filtered to remove enzyme. Isoalpha acids and dihydro-(rho)-isoalpha acids are quantified by HPLC.

Example 3—Enzyme Treatment of Acidified Hop Derived Isoalpha Acids with Cofactor Recycling by Isopropanol Oxidation Isoalpha acids are treated in a manner described in Example 2, where the source of isoalpha acids is a highly concentrated material (68.9% isoalpha acids) having a pH <7.

Example 4—Enzyme Treatment of Hop Derived Isoalpha Acids with Cofactor Recycling by Glucose Dehydrogenase Isoalpha acids are treated in a manner described in Example 2, with the exception that isopropanol is replaced with 4.3 U/mL Glucose Dehydrogenase, 0.7 g/L mM NAD, and 14.4 g/L D-glucose.

Example 5—Enzyme Treatment of Hop Derived Isoalpha Acids without Cofactor Recycling Isoalpha acids are treated in a manner described in Example 2, with the exception that isopropanol is replaced with an equimolar amount of NADPH as substrate.

Example 6—Enzyme Treatment of Hop Derived Isoalpha Acids with Thermostable Reductase Naturally thermostable reductases are obtained from thermophilic bacterial and archaeal organisms, such as *Thermotoga maritima*. In a 1.5 mL microcentrifuge tube, 100 uL enzyme solution (1.5-15.0 mg/mL enzyme) is added to 900 uL of buffered aqueous solution (263 mM Sodium Phosphate pH 7.0, 1.7 mM magnesium sulfate, 4.3 U/mL Glucose Dehydrogenase, 1.1 mM NADP+, 1.1 mM NAD+, 80 mM D-glucose). ISOLONE® Isomerized Hop Extract solution (29% isoalpha acids) is added for a final concentration of 0.145-16% isoalpha acids. The reaction is incubated at 60-80° C. with orbital shaking at 180 rpm for 24 hours. The obtained reaction mixture is filtered to remove enzyme.

Example 7—Enzyme Treatment of Hop Derived Isoalpha Acids with Cofactor Recycling by Ethanol Oxidation Isoalpha acids are treated in a manner described in Example 2, with the exception that isopropanol is replaced with ethanol.

Example 8—Enzyme Treatment of Hop Derived Isoalpha Acids with Immobilized Ketoreductase via $SiO_2$ A ketoreductase is adsorbed on $SiO_2$ and crosslinked with glutaraldehyde to yield an immobilized ketoreductase material. Isoalpha acids are treated with the immobilized ketoreductase in a manner described in Example 2. The obtained reaction mixture is centrifuged at 10,000 g to remove immobilized enzyme.

Example 9—Enzyme Treatment of Hop Derived Isoalpha Acids with Immobilized Ketoreductase via DEAE-Cellulose A ketoreductase is crosslinked with glutaraldehyde and adsorbed onto DEAE-cellulose to yield an immobilized ketoreductase material. Isoalpha acids are treated with the immobilized ketoreductase in a manner described in Example 2. The obtained reaction mixture is centrifuged at 10,000 g to remove immobilized enzyme.

Example 10—Enzyme Treatment of Hop Derived Isoalpha Acids with Immobilized Ketoreductase via PEI-Treated Alumina A ketoreductase is crosslinked with glutaraldehyde and adsorbed onto polyethylimine (PEI)-treated alumina to yield an immobilized ketoreductase material. Isoalpha acids are treated with the immobilized ketoreductase in a manner described in Example 2. The obtained reaction mixture is centrifuged at 10,000 g to remove immobilized enzyme.

Example 11—Enzyme Treatment of Hop Derived Isoalpha Acids with Co-Immobilized Enzymes A reductase and cofactor recycling enzyme, such as glucose dehydrogenase, are immobilized sequentially or together in a single composition utilizing any of the abovementioned methods to yield a coimmobilized material. Coimmobilized material is added to a concentration of 0.1-10 mg/mL in buffered aqueous solution (50-250 mM sodium phosphate, 0.1-1.0 mM NADPH, 10-40% isopropanol, pH 7-9). ISOLONE® Isomerized Hop Extract solution (29% isoalpha acids) is added for a final concentration of 0.145-16% isoalpha acids. The reaction is incubated at 30-40° C. with orbital shaking at 180 rpm for 24 hours. The obtained reaction mixture is centrifuged at 10,000 g to remove immobilized enzyme.

Example 12—Enzyme Treatment of Hop Derived Isoalpha Acids with Crosslinked/Spheronized Cells A cell (bacterial, fungal, plant) expressing the reductase is crosslinked with polyamine/glutaraldehyde, extruded and spheronized to yield an immobilized reductase material. Immobilized reductase is added to a concentration of 0.1-10 mg/mL in buffered aqueous solution (50-250 mM sodium phosphate, 0.1-1.0 mM NADPH, 10-40% isopropanol, pH 7-9). ISOLONE® Isomerized Hop Extract solution (29% isoalpha acids) is added for a final concentration of 0.145-16% isoalpha acids. The reaction is incubated at 30-40° C. with orbital shaking at 180 rpm for 24 hours. The obtained reaction mixture is centrifuged at 10,000 g to remove immobilized enzyme.

Example 13—Enzyme Treatment of Hop Derived Isoalpha Acids with Crosslinked/Entrapped Cells A cell (bacterial, fungal, plant) expressing the reductase is crosslinked with glutaraldehyde and entrapped within gelatin or polymer beads to yield an immobilized reductase material. Immobilized reductase is added to a concentration of 0.1-10 mg/mL in buffered aqueous solution (50-250 mM sodium phosphate, 0.1-1.0 mM NADPH, 10-40% isopropanol, pH 7-9). ISOLONE® lsomerized Hop Extract solution (29% isoalpha acids) is added fora final concentration of 0.145-16% isoalpha acids. The reaction is incubated at 30-40° C. with orbital shaking at 180 rpm for 24 hours. The obtained reaction mixture is centrifuged at 10,000 g to remove immobilized enzyme.

Example 14—Enzyme Treatment of Hop Derived Isoalpha Acids with Living Cells

A microorganism (bacteria, fungus) expressing the reductase is grown via fermentation to high density, harvested, washed, and pelleted to form cell paste. Cell paste is resuspended in fresh growth media containing 0.145-16% isoalpha acids. The cell culture is incubated at 25-37° C. with mixing for 24-72 hours. The cell culture is centrifuged at 10,000 g to remove cells from spent growth media. Dihydro-(rho)-isoalpha acids are extracted from the spent growth media with ethanol.

Example 15—Enzyme Treatment of Hop Derived Isoalpha Acids with Cell Lysate

A microorganism (bacteria, fungus) expressing the reductase is grown via fermentation to high density, harvested, washed, and lysed to yield a crude cell lysate. Isoalpha acids are added to the crude cell lysate to a final concentration of 0.145-16% isoalpha acids. The cell culture is incubated at 25-40° C. with mixing for 24 hours. The reaction mixture is centrifuged at 10,000 g or filtered to

Example 16—Enzyme Treatment of Hop Derived Isoalpha Acids with Psychrophilic Reductase Enzyme treatment where the reductase is a homolog from a psychrophilic (cold tolerant) microorganism. Reductase is added to a concentration of 0.1-10 mg/mL in buffered aqueous solution (50-250 mM sodium phosphate, 0.1-1.0 mM NADPH, 10-40% isopropanol, pH 7-9). ISOLONE® Isomerized Hop Extract solution (29% isoalpha acids) is added for a final concentration of 0.145-16% isoalpha acids. The reaction is incubated at 0-20° C. with orbital shaking at 180 rpm for 24 hours. The obtained reaction mixture is filtered to remove enzyme.

Example 17—Enzyme Treatment of Hop Derived Isoalpha Acids with NADH Cofactor Recycling Enzyme treatment where the NADPH cofactor is substituted with NADH. Isoalpha Acids are treated in a manner described in Example 2 but the NADP is replaced with NAD.

Example 18—Enzyme Treatment of Hop Derived Isoalpha Acids with Cofactor Recycling via Ethanol Oxidation Enzyme treatment where the isopropanol starting material is substituted with ethanol, wherein a reductase is added to a concentration of 0.1-10 mg/mL in buffered aqueous solution (50-250 mM sodium phosphate, 0.1-1.0 mM NADH, 10-40% ethanol, pH 7-9). ISOLONE® Isomerized Hop Extract solution (29% isoalpha acids) is added for a final concentration of 0.145-16% isoalpha acids. The reaction is incubated at 30-40° C. with orbital shaking at 180 rpm for 24 hours. The obtained reaction mixture is filtered to remove enzyme.

Example 19—Enzyme Treatment of Hop Derived Isoalpha Acids Followed by Extraction Enzyme treatment followed by extraction to increase final concentration of dihydro-(rho)-isoalpha acids. Isoalpha acids are treated in a manner described in Example 2. The obtained reaction mixture is filtered to remove enzyme and extracted with food-grade solvent to achieve a desired concentration of dihydro-(rho)-isoalpha acids.

Example 20—Enzyme Treatment of Hop Derived Isoalpha Acids Followed by Thermal Inactivation Isoalpha acids are treated in a manner described in Example 2. The reaction is incubated at 30-40° C. with orbital shaking at 180 rpm for 24 hours. The obtained reaction mixture is heated at 80-100° C. for 10-30 minutes to inactivate enzyme.

Example 21—Enzyme Treatment of Hop Derived Isoalpha Acids Followed by Chemical Inactivation Isoalpha acids are treated in a manner described in Example 2. The reaction is incubated at 30-40° C. with orbital shaking at 180 rpm for 24 hours. Food-grade ethanol is added to a final concentration of >50% to inactivate enzyme.

Example 22—Enzyme Treatment of Hop Derived Isoalpha Acids with Immobilized Ketoreductase Recycling A ketoreductase is crosslinked with glutaraldehyde and absorbed onto DEAE-cellulose to yield an immobilized ketoreductase material. Isoalpha acids are then treated with the immobilized ketoreductase in a manner described in Example 2. The obtained reaction mixture is centrifuged at 10,000 g to separate immobilized ketoreductase from the reaction solution. Immobilized ketoreductase is recovered, washed with water or aqueous buffer, and re-used in a new reaction mixture.

Conclusions 23 ketoreductases have been characterized as transforming isoalpha acids into dihydro-(rho)-isoalpha acids. The ketoreductases characterized in this study possess an enzymatic activity that has not been described previously. The ketoreductases characterized in this study all reduce a ketone group into an alcohol and are thus ketoreductases. These results demonstrate that a ketoreductase biocatalyst may be employed to convert isoalpha acids to dihydro-(rho)-isoalpha acids in a novel biotransformation process. The present invention replaces current chemical processes utilizing sodium borohydride.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference.

CITED REFERENCES

1. *Sodium Borohydride;* MSDS No. S9125; Sigma-Aldrich Co.: Saint Louis, MO Nov. 1, 2015. (accessed Jun. 8, 2017).
2. Robinson, P. K., Enzymes: principles and biotechnological applications. Essays Biochem 2015, 59, 1-41.
3. Hult, K.; Berglund, P., Enzyme promiscuity: mechanism and applications. Trends Biotechnol. 2007, 25 (5), 231-238.
4. Nobeli, I.; Favia, A. D.; Thornton, J. M., Protein promiscuity and its implications for biotechnology. Nat. Biotechnol. 2009, 27 (2), 157-167.
5. Pozen, M., Enzymes in Brewing. Ind. Eng. Chem, 1934, 26 (11), 1127-1133.
6. Praet, T.; Opstaele, F.; Jaskula-Goiris, B.; Aerts, G.; De Cooman, L., Biotransformations of hop-derived aroma compounds by *Saccharomyces cerevisiae* upon fermentation. Cerevisia, 2012, 36, 125-132.
7. Wallerstein, L. (1947) Bentonite and Proteolytic Enzyme Treatment of Beer, U.S. Pat. No. 2,433,411.
8. Ghionno, L.; Marconi, O.; Sileoni, V.; De Francesco, G.; Perretti, G., Brewing with prolyl endopeptidase from *Aspergillus niger:* the impact of enzymatic treatment on gluten levels, quality attributes, and sensory profile. Int. J. Food Sci. Technol, 2017, 52 (6), 1367-1374.
9. Gros, J.; Tran, T. T. H.; Collin, S., Enzymatic release of odourant polyfunctional thiols from cysteine conjugates in hop. J. Inst. Brew. 2013, 119 (4), 221-227.

The invention claimed is:

1. A process for the preparation of dihydro-(rho)-isoalpha acids, comprising treating isoalpha acids with a ketoreductase enzyme or a microorganism expressing a gene that encodes the ketoreductase, wherein the ketoreductase enzyme comprises an amino acid sequence selected from the group consisting of SEQ ID NO: 16 and SEQ ID NO: 19, or wherein the ketoreductase enzyme or microorganism expressing a gene which encodes the ketoreductase is 99, 95 or 90 percent homologous to the ketoreductase enzyme selected from the group consisting of SEQ ID NO: 16 and SEQ ID NO: 19.

2. The process according to claim 1, wherein the process is carried out in an aqueous system.

3. The process according to claim 2, wherein the process is carried out under mild temperature and pH conditions.

4. The process according to claim 1, comprising adding the ketoreductase enzyme and NADPH or NADP to a mixture of isoalpha acids followed by incubation.

5. The process according to claim 1, comprising adding the ketoreductase enzyme and NADPH or NADP to a mixture of isoalpha acids in the presence of isopropanol for cofactor recycling, followed by incubation.

6. The process according to claim 5, wherein the concentration of isoalpha acids, i.e. the substrate, is maximized to increase the volumetric productivity of the bioconversion.

7. The process according to claim 5, wherein the concentration of the cofactor NADPH or NADP in the mixture is minimized to improve the economics of the bioconversion.

8. The process according to claim 1, comprising adding the ketoreductase enzyme and NADPH or NADP to a mixture of isoalpha acids in the presence of another enzyme for cofactor recycling, followed by incubation.

9. The process according to claim 1, comprising adding a whole cell biocatalyst, wherein the whole cell biocatalyst is an immobilized microorganism expressing the gene which encodes a ketoreductase, to a mixture of isoalpha acids followed by incubation.

10. The process according to claim 1, comprising culturing a microorganism expressing the gene which encodes the ketoreductase and adding isoalpha acids to the culture.

11. The process according to claim 1, comprising adding the ketoreductase enzyme, wherein the ketoreductase is thermostable, to an extract of isoalpha acids wherein heat is applied, and the mixture is incubated.

12. The process according to claim 1, wherein the ketoreductase specifically reduces cis-isohumulone, cis-isocohumulone, and cis-isoadhumulone.

13. The process according to claim 1, wherein the ketoreductase specifically reduces trans-isohumulone, trans-isocohumulone, and trans-isoadhumulone.

14. The process according to claim 1, comprising adding a mixture of 2 or more ketoreductase enzymes in an amount effective to reduce a mixture of cis- and trans-isoalpha acids, to their respective dihydroisoalpha acids.

15. The process according to claim 14, wherein the mixture of 2 or more ketoreductase enzymes produces a unique mixture of dihydroisoalpha acids that is distinct from that produced by chemical reducing agents.

16. The process according to claim 1, wherein the ketoreductase is 99 or 95 percent homologous to the ketoreductase of SEQ ID NO:16 or SEQ ID NO:19.

17. The process according to claim 15, wherein the mixture of 2 or more ketoreductase enzymes produces a unique mixture of dihydroisoalpha acids that is distinct from that produced by sodium borohydride.

* * * * *